(12) United States Patent
Ciccarone et al.

(10) Patent No.: US 9,879,243 B2
(45) Date of Patent: Jan. 30, 2018

(54) CULTURE MEDIUM FOR CELL GROWTH AND TRANSFECTION

(71) Applicant: LIFE TECHNOLOGIES CORPORATION, Carlsbad, CA (US)

(72) Inventors: Valentina C. Ciccarone, Gaithersburg, MD (US); Dale Gruber, Leesburg, FL (US); Shelly Bennett, North Bethesda, MD (US)

(73) Assignee: LifeTechnologies Corporation, Carlsbad, CA (US)

( * ) Notice: Subject to any disclaimer, the term of this patent is extended or adjusted under 35 U.S.C. 154(b) by 0 days.

(21) Appl. No.: 13/968,157

(22) Filed: Aug. 15, 2013

(65) Prior Publication Data

US 2014/0057335 A1    Feb. 27, 2014

Related U.S. Application Data

(63) Continuation of application No. 11/552,783, filed on Oct. 25, 2006, now abandoned, which is a continuation of application No. 10/105,937, filed on Mar. 26, 2002, now abandoned.

(60) Provisional application No. 60/278,754, filed on Mar. 27, 2001.

(51) Int. Cl.
| C12N 15/63 | (2006.01) |
| C12N 15/11 | (2006.01) |
| C12N 15/113 | (2010.01) |
| C12N 9/38 | (2006.01) |
| C12N 15/88 | (2006.01) |
| C12N 5/00 | (2006.01) |

(52) U.S. Cl.
CPC ........... *C12N 9/2471* (2013.01); *C12N 5/005* (2013.01); *C12N 5/0018* (2013.01); *C12N 5/0043* (2013.01); *C12N 15/88* (2013.01); *C12N 2500/22* (2013.01); *C12N 2500/24* (2013.01); *C12N 2501/999* (2013.01); *C12N 2510/02* (2013.01)

(58) Field of Classification Search
None
See application file for complete search history.

(56) References Cited

U.S. PATENT DOCUMENTS

| 2,695,314 | A | 11/1954 | Kusmln |
| 2,901,461 | A | 8/1959 | Auerbach et al. |
| 3,152,188 | A | 10/1964 | Kirkpatrick et al. |
| 4,673,649 | A | 6/1987 | Boyce et al. |
| 4,897,355 | A | 1/1990 | Eppstein et al. |
| 4,940,666 | A | 7/1990 | Boyce et al. |
| 5,045,454 | A | 9/1991 | Bertheussen |
| 5,118,513 | A | 6/1992 | Mehansho et al. |
| 5,135,866 | A | 8/1992 | Heifetz et al. |
| 5,166,066 | A | 11/1992 | Carter |
| 5,171,678 | A | 12/1992 | Behr et al. |
| 5,208,036 | A | 5/1993 | Eppstein et al. |
| 5,232,848 | A | 8/1993 | Wolfe et al. |
| 5,279,833 | A | 1/1994 | Rose |
| 5,283,185 | A | 2/1994 | Epand et al. |
| 5,334,761 | A | 8/1994 | Gebeyehu et al. |
| 5,455,335 | A | 10/1995 | Kahne et al. |
| 5,459,127 | A | 10/1995 | Felgner et al. |
| 5,474,931 | A | 12/1995 | DiSorbo et al. |
| 5,545,412 | A | 8/1996 | Eppstein et al. |
| 5,550,289 | A | 8/1996 | Eppstein et al. |
| 5,589,466 | A | 12/1996 | Felgner et al. |
| 5,627,159 | A * | 5/1997 | Shih ..................... A61K 9/1272 424/450 |
| 5,667,774 | A | 9/1997 | Figuly |
| 5,674,908 | A | 10/1997 | Haces et al. |
| 5,703,055 | A | 12/1997 | Felgner et al. |
| 5,705,385 | A | 1/1998 | Bally et al. |
| 5,713,055 | A | 1/1998 | Joel |
| 5,719,131 | A | 2/1998 | Harris et al. |

(Continued)

FOREIGN PATENT DOCUMENTS

| EP | 0282942 | 9/1988 |
| EP | 0394111 | 10/1990 |

(Continued)

OTHER PUBLICATIONS

Sigma-Aldrich, "Classic Plant Media", Sigma-Aldrich, retrieved from internet, URL: http://www.sigmaaldrlch.com/life-science/molecular-biology/plantbiotechnology/tissue-culture-protocols/classic_plant_media.html, 1 Pg, Oct. 22, 2009.

(Continued)

*Primary Examiner* — Maria Marvich

(57) ABSTRACT

The present invention is directed generally to cell culture media useful for introducing macromolecules and compounds (e.g., nucleic acid molecules) into cells (e.g., eukaryotic cells) in the presence of said media. Cells containing introduced materials can be further cultured in the media. In particular, the invention allows introduction of nucleic acid molecules (e.g., vectors) into cells (particularly eukaryotic cells) and expression of proteins encoded by the nucleic acid molecules in the cells. The invention obviates the need to change the cell culture medium each time a different procedure is performed with the cells (e.g., culturing cells vs. transfecting cells). The invention thus provides efficient and high throughput methods to transform/transfect culture and cells avoiding the need for multiple manipulations and transfers of cells during transfection and expression studies.

2 Claims, 7 Drawing Sheets

(56) References Cited

U.S. PATENT DOCUMENTS

Figure 1A:
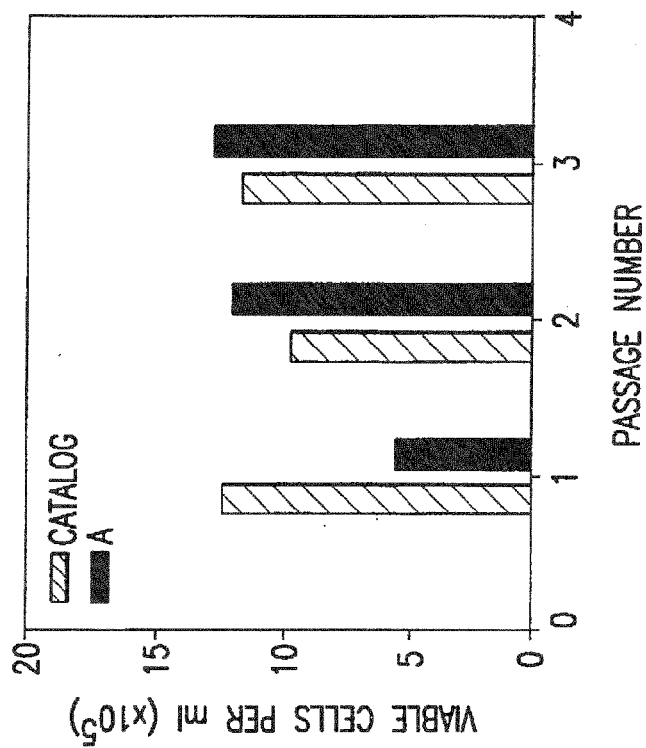

| | | | |
|---|---|---|---|
| 5,736,392 A | 4/1998 | Hawley-Nelson et al. | |
| 5,744,335 A | 4/1998 | Wolff et al. | |
| 5,753,613 A | 5/1998 | Ansell et al. | |
| 5,783,565 A | 7/1998 | Lee et al. | |
| 5,783,566 A | 7/1998 | Mislick | |
| 5,785,992 A | 7/1998 | Ansell et al. | |
| 5,793,566 A | 8/1998 | Scura et al. | |
| 5,795,587 A | 8/1998 | Gao et al. | |
| 5,830,430 A | 11/1998 | Unger et al. | |
| 5,830,878 A | 11/1998 | Gorman et al. | |
| 5,834,439 A | 11/1998 | Haces et al. | |
| 5,837,283 A | 11/1998 | McDonald et al. | |
| 5,840,710 A | 11/1998 | Lee et al. | |
| 5,908,635 A | 6/1999 | Thierry | |
| 5,935,936 A | 8/1999 | Fasbender et al. | |
| 5,948,767 A | 9/1999 | Scheule et al. | |
| 5,948,925 A | 9/1999 | Keynes et al. | |
| 5,962,533 A | 10/1999 | Bergeron, Jr. | |
| 6,093,564 A | 7/2000 | Budowsky | |
| 6,103,529 A | 8/2000 | Price et al. | |
| 6,171,862 B1 | 1/2001 | Abe et al. | |
| 6,506,604 B2 | 1/2003 | Finer et al. | |
| 6,541,225 B1 | 4/2003 | Li | |
| 6,544,790 B1 | 4/2003 | Sabatini | |
| 6,767,741 B1 | 7/2004 | Epstein et al. | |
| 7,026,454 B1 | 4/2006 | Shah | |
| 2003/0032203 A1 | 2/2003 | Sabatini et al. | |
| 2003/0073116 A1* | 4/2003 | Ginsburg et al. | 435/6 |
| 2004/0038862 A1 | 2/2004 | Goodwin et al. | |
| 2005/0100940 A1 | 5/2005 | Holtzman et al. | |
| 2005/0118253 A1 | 6/2005 | MacLachlan et al. | |
| 2007/0025952 A1 | 2/2007 | Davis et al. | |
| 2007/0254358 A1 | 11/2007 | Ciccarone et al. | |

FOREIGN PATENT DOCUMENTS

| | | |
|---|---|---|
| EP | 0846680 | 6/1998 |
| GB | 0901673 | 7/1962 |
| WO | WO-1988/02774 | 4/1988 |
| WO | WO-1993/000423 | 1/1993 |
| WO | WO-1994/27435 | 12/1994 |
| WO | WO-1995/17373 | 6/1995 |
| WO | WO-1997/42819 | 11/1997 |
| WO | WO-1998/02190 | 1/1998 |
| WO | WO-1998/08934 | 3/1998 |
| WO | WO-1998/15614 | 4/1998 |
| WO | WO-1998/19709 | 5/1998 |
| WO | WO-1998/29541 | 7/1998 |
| WO | WO-1998/040499 | 9/1998 |
| WO | WO-1998/040502 | 9/1998 |
| WO | WO-1999/29712 | 6/1999 |
| WO | WO-2000/27795 | 5/2000 |
| WO | WO-2001/16294 | 3/2001 |

OTHER PUBLICATIONS

Sigma-Aldrich, "Formulations of commonly used Insect media", retrieved from the Internet, http://www.sigmaaldrich.com, 5 Pgs, Oct. 22, 2009.

Atlas, R M. et al., "Sources of Media", *Handbook of Microbiological Media*, 1997.

Ausubel, F. et al., "Current Protocls in Molecular Biology", *Chapter 9, John Wiley and Sons*, 1998.

Ausubel, Frederick et al., "Introduction of DNA Into Mammalian Cells", *in Current Protocols in Molecular Biology*, Chapter 9, Ausubel, F. , et al., eds. John Wiley and Sons, Inc. , New York, NY, 1996, 9.0.1-9.17.3.

Barnes,, et al., "Cell Culture Methods for Molecular and Cell Biology,", *Methods for Preparation of Media, Supplements and Substrate for Serum-Free Animal Cell Culture,*, vol. 1, Barnes, D.W., et al., eds., New York, NY, Alan R. Liss, Inc., 1984, pp. 23-68.

Barritault, D. et al., "Is There a Ubiquitous Growth Factor in the Eye? Proliferation Induced in Different Cell Types by Eye-Derived Growth Factors", *Differentiation*, vol. 18, 1981, 29-42.

Battista, P. J. et al., "Serum-free media for the culture of chinese hamster ovary cells", *Am. Biotechnol. Lab. 12*, International Scientific Communications Inc., 1994, 64-68.

Behr, Jean-Paul et al., "Efficient Gene Transfer Into Mammalian Primary Endocrine Cells with Lipopolyamine-Coated DNA", *Proceedings of the National Academy of Sciences (PNAS)*, vol. 86, Sep. 1989, 6982-6986.

Berg, D. T. et al., "High-Level Expression of Secreted Proteins from Cells Adapted to Serum-Free Suspension Culture", *BioTechniques*, vol. 14, No. 6, 1993, 972-978.

Bout, A et al., "Improved helper cells for RCA-free production of E1-deleted recombinant adenovirus vectors", *Conference Supplement: Cancer Gene Therapy*, vol. 3, No. 6, Abstract No. P-52, Appleton & Lange, 1996, S24.

Boyce, S. et al., "Calcium-regulated differentiation of normal human epidermal keratinocytes in chemically defined clonal culture and serum-free serial culture", *J. Invest. Dermatol*, vol. 81, 1983, 33s-40s.

Ciccarone, et al., "Lipofectamine 2000 Reagent for Rapid, Efficient Transfection of Eukaryotic Cells", *Focus*, vol. 21, No. 2, 1999, 54-55.

Cohen, S. , "Isolation of a Mouse Submaxillary Gland Protein Accelerating Incisor Eruption and Eyelid Opening in the New-born Animal", *The Journal of Biological Chemistry*, vol. 237, No. 5, 1962, 1555-1562.

Coleman, W H. et al., "Inhibitors of Animal Cell-Free Protein Synthesis from Grains", *Biochim. Biophys. Acta*, vol. 696, 1982, 239-244.

Daley, J. et al., "Growth of human epidermal keratinocytes in keratinocyte serum-free medium.", *Focus*, vol. 12(3), Aug. 2, 1990, 68-71.

Derwent, , "Derwent WPI English language abstract", *Dialog File 351*, Accession No. 1203773, Derwent Information Ltd., 1974.

DMEM, , "DMEM Ham's F12 Solution", Sep. 15, 2005.

EP 98903438 Supplementary Partial European Search Report dated Aug. 10, 2004.

EP02723601 Supplementary Partial European Search Report Completed Mar. 19, 2004.

Felgner, Philip L. et al., "Lipofection: A Highly Efficient, Lipid-Mediated DNA Transfection Procedure", *Proceedings of the National Academy of Sciences (PNAS)*, vol. 84, 1987, 7413-7417.

Freshney, R. , "Introduction", *Culture of Epithelial Cells*, Freshney, R.I., ed., Wiley-Liss, Inc., New York, NY, 1992, 1-23.

Freshney, R. I. , "Propagation in Suspension Culture of Animal Cells", *A Manual of Basic Technique*, 1st ed., Freshney, R.I., ed., Alan R. Liss, Inc., New York, NY, 1983, 123-125.

Ganeshaguru, K. et al., ""Effect of Various Iron Chelating Agents on DNA Synthesis in Human Cells,"", *Biochem. Pharmacol.* 29, Pergamon Press Ltd., 1980, 1275-1279.

Gao, Xiang et al., "A Novel Cationic Liposome Reagent for Efficient Transfection of Mammalian Cells", *Biochemical and Biophysical Research Communications*, vol. 179, Aug. 30, 1991, 280-285.

Garnier, A. et al., "Scale-up ofthe adenovirus expression system for the production of recombinant protein in human 293s cells", *Cytotechnolology*, vol. 15, 1994, 145-155.

George, E.F. et al., "Plant Culture Media, vol. 1 Formulations and Uses", Exegetics Ltd. Edington, Westbury, Wilts, BA13 4QG England, 1987.

Gilchrest, B. et al., "Characterization and Partial Purification of Keratinocyte Growth Factor From the Hypothalamus", *Journal of Cellular Physiology*, vol. 120, 1984, 377-383.

Goldstein, et al., "Enhanced transfection efficiency and improved cell survival after electroporation of G2/M-synchronized cells and treatment with sodium butyrate", *Nucleic Acid Research*, vol. 17, No. 10, 1989, 3959-3971.

Gorfien, "Recombinant Protein Production by CHO Cells Cultured in a Chemically Defined Medium", *Animal Cell Technology: Basic and Applied Aspects 9*, Springer, Jan. 1998, 247-252.

Gospodarowicz, D. , "Preparations and Uses of Lipoproteins to Culture Normal Diploid and Tumor Cells Under Serum-Free Con-

(56) References Cited

OTHER PUBLICATIONS ditions", *Methods for Preparation of Media, Supplements, and Substrata for Serum-Free Animal Cell Culture*, Barns, D. W., et al., eds., Alan R. Liss, Inc., New York, NY,, 1984, 69-86.
Invitrogen, "Eukaryotic Transfections with Cationic Lipid Reagents", 2nd ed, Life Techonologies, 1999.
Invitrogen, "FreeStyle 293 Expression Medium", *GIBCO Invitrogen Corporation*, www.invitrogen.com/contents/sfs/manuals/3945.pdf, 2004, 1-2.
Invitrogen, "Guide to Eukaryotic Transfections with Cationic Lipid Reagents", *Life Technologies/Gibco BRL Technical Bulletin*, Now Invitrogen, Corp., Mar. 18, 2004, 1-32.
Invitrogen, "Transfection Protocols, CHO-S in Suspension with DMRIE C Reagent", *In Invitrogen Life Technologies Catalog*, 2000.
Invitrogen Corporation, "293Fection product profile sheet", 2002.
Invitrogen Corporation, "Lipofectomine 2000 Product Profile Sheet", 2003.
Kao, F. T. et al., "Genetics of Somatic Mammalian Cells, VII. Induction and Isolation of Nutritional Mutants in Chinese Hamster Cells", *Proceedings of the National Academy of Sciences (PNAS)*, vol. 60, 1968, 1275-1281.
Keay, Leonard , "Autoclavable Low Cost Serum-Free Cell Culture Media. The Growth of L Cells and BHK Cells on Peptones", vol. 17, No. 5, *Biotechnology and Bioengineering*, 1975, 745-764.
Keay, Leonard , "The Growth of L-Cells and Vero Cells on an Autoclavable MEM-Peptone Medium", *Biotechnology and Bioengineering*, vol. 19, John Wiley & Sons, Inc., 1977, 399-411.
Keenan, J., et al., "Replacement of Transferrin by Simple Iron Compounds for MDCK Cells Grown and Subcultured in Serum-Free Medium", In Vitro *Cell Dev. Biol.—Animal*, vol. 32, Society for In Vitro Biology, 1996, 451-453.
Kyung, Yun-Seung , "High density culture of mammalian cells with dynamic perfusion based on on-line oxygen uptake rate measurements", *Cytotechnology*, vol. 14, 1994, 183-190.
Lambert, K. et al., "Cell Growth Media", *Animal Cell Biotechnology*, vol. 1, Spier, R.E. and Griffiths, J.B., eds, Academic Press, inc., London, 1985, 85-122.
Lasfargues, E. Y. et al., "A Serum Substitute That Can Support the Continuous Growth of Mammary Tumor Cells", In Vitro, Vol, vol. 8, No. 6, 1973, 494-500.
Life Technologies, "Guide to Eukaryotic Transfections with Cationic Lipid Reagents", *Life Technologies* 2nd Edition, 1999, 1-36.
Life Technologies, , "Life Technologies Catalogue and Reference Guide", 2001, 25-1-25-11.
Maciag, T. et al., "An Endocrine Approach to the Control of Epidermal Growth: Serum-Free Cultivation of Human Keratinocytes.", *Science*, vol. 211, 1981, 1452-1454.
Maciag, T. et al., "An endothelial cell growth factor from bovine hypothalamus: identification and partial characterization.", *Proceedings of the National Academy of Sciences (PNAS)*, vol. 76, No. 11, 1979, 5674-5678.
Mounkes, et al., "Proteoglycans Mediate Cationic Liposome-DNA Complex-based Gene Delivery in Vitro and in Vivo", *The Journal of Biological Chemical*, vol. 273(40), Issue of Oct. 2, 1998, 26164-26170 pgs.
Palermo, D. P. et al., "Production of Analytical Quantities of Recombinant Proteins in Chinese Hamster Ovary Cells Using Sodium butyrate to Elevate Gene Expression", *J. Biotechnol.*, 1991, 35-48.
Peehl, D. et al., "Growth and Differentiation of Human Keratinocytes Without a Feeder Layer or Conditioned Medium", In Vitro, vol. 16(6), 1980, 516-525.
Peshwa, M. et al., "Cultivation of Mammalian Cells as Aggregates in Bioreactors: Effect of Calcium Concentration on Spatial Distribution of Viability", *Biotechnol. Bioeng 41*, John Wiley & Sons, Inc., 1993, 179-187.
Pichet, et al., "High Throughput Transfection in 96-Well Plates with Lipofectamine 2000", *The FASEB Journal*, vol. 14, No. 8, 2000, A1473.
Pichet, et al., "Transfection of Mammalian Cells in 96 Well Plates with Lipofectamine 2000 Reagent", *Focus*, vol. 21(3), 1999, 58-61.
Pirisi, L. et al., "Transformation of human fibroblasts and keratinocytes with human papilomavirus type 16 DNA", *J. Virol.,*, vol. 61, No. 4, American Society for Microbiology, 1987, 1061-1066.
Pittelkow, M. et al., "New techniques for the in vitro culture of human skin keratinocytes and perspectives on their use for grafting of patients with extensive burns.", *Mayo Clin. Proc*, vol. 61, Mayo Foundation, 1986, 771-777.
Qian, Z. M. et al., "Mechanisms of iron uptake by mammalian cells", *Biochimica et Biophysica Acta*, vol. 1269, Elsevier Science B.V., 1995, 205-214.
Ringer, S. , "Concerning the Influence Exerted by Each of the Constituents of the Blood on the Contraction of the Ventricle", *Journal of Physiology*, vol. 3, 1882, 380-393.
Rosenthal, A. F. et al., "A Synthetic Inhibitor of Venom Lecithinase A", *J. Biol. Chem.*, vol. 235, 1960, 2202-2206.
Roy, et al., "High Transfection Efficiency of Cloned Cell Lines", *Focus*, vol. 20(3), 1999, 62-63.
Schifferli, et al., "Transfection of Suspension Cultures of CHO Cells", [same as FIP ref #287707] *FOCUS Gene Expression Research and Development Life Technologies, Inc.* (Rockville, MD), vol. 21, No. 1, 1999, 16-17.
Schlaeger, Ernst J. , "The Protein Hydrolysate, Primatone RL, is a Cost-Effective Multiple Growth Promoter of Mammalian Cell Culture in Serum-Containing and Serum-Free Media and Displays Anti-Apoptosis Properties", *Journal of Immunological Methods*, vol. 194, No. 2, Aug. 14, 1996, 191-199.
Shipley, G. et al., "Control of Growth and Differentiation In Vitro ot Human Keratinocytes Cultured in Serum-free Medium", *Arch. Dermatol.*, vol. 123, 1987, 1541a-1544a.
Shipley, G. et al., "Growth of Normal Human Keratinocytes and Fibroblasts in Serum-Growth of Normal Human Keratinocytes and Fibroblasts in Serum-Free Medium is Simulated by Acidic and Basic Fibroblast Growth Factor", *J. Cell. Physiol.*, vol. 138, 1989, 511-518.
Terashima, M. et al., Effect of osmotic pressure on human α1-antitrypsin production by plant cell culture, *Biochem, Eng. J.*, vol. 4,, 1999, 31-36.
Testa, U. et al., "The iron-chelating agent picolinic acid enhances transferring receptors expression in human erythroleukaemic cell lines", *Brit. J. Haematol. 60*, Blackwell Scientific Publications, 1985, 491-502.
Wang, Jia-Wang et al., "Establishment of Three Adenovirus Packaging Cell Lines", *Conference Supplement: Cancer Gene Therapy*, vol. 3, No. 6, Abstract No. P-53, Appleton & Lange, Nov. 1996, S24.
Waymouth, C. , "Ch. 3, Construction and use of Synthetic Media", *Cells and Tissues in Culture: Methods, Biology and Physiology*, vol. 1, Willmer, E.N., Ed., Academic Press, 1965, 99-142.
Waymouth, C. , "Osmolality of Mammalian Blood and of Media for Culture of Mammalian Cells", In Vitro *Journal of the Tissue Culture Association*, vol. 6, No. 2, 1970, 109-127.
Waymouth, C. , "Preparation and Use of Serum-Free Culture Media", *Methods for Preparation of Media, Supplements, and Substrata for Serum-Free Animal Cell Culture*, Barnes, D.W., et al., eds., Wiley-Liss, Inc., New York, NY, 1984, 23-68.
White, G. P. et al., "The Effect of Chelating Agents on Iron Mobilization in Chang Cell Cultures", *Blood*, vol. 48, Grune & Stratton, 1976, 923-929.
Wille, J. et al., "Integrated control of growth and differentiation of normal human prokeratinocytes cultured in serum-free medium: clonal analyses, growth kinetics, and cell cycle studies", *J. Cell Physiol.*, vol. 121, 1984, 31-44.
Zang, Michael et al., "Production of Recombinant Proteins in Chinese Hamster Ovary Cells Using a Protein Free Cell Culture Medium", *Bio/Technology*, vol. 13, Apr. 13, 1995, 389-392.
Zhou, Xiaohuai et al., "Lipophilic Polylysines Mediate Efficient DNA Transfection in Mammalian Cells", *Biochimica et Biophysica Acta*, vol. 1065, 1991, 8-14.

\* cited by examiner

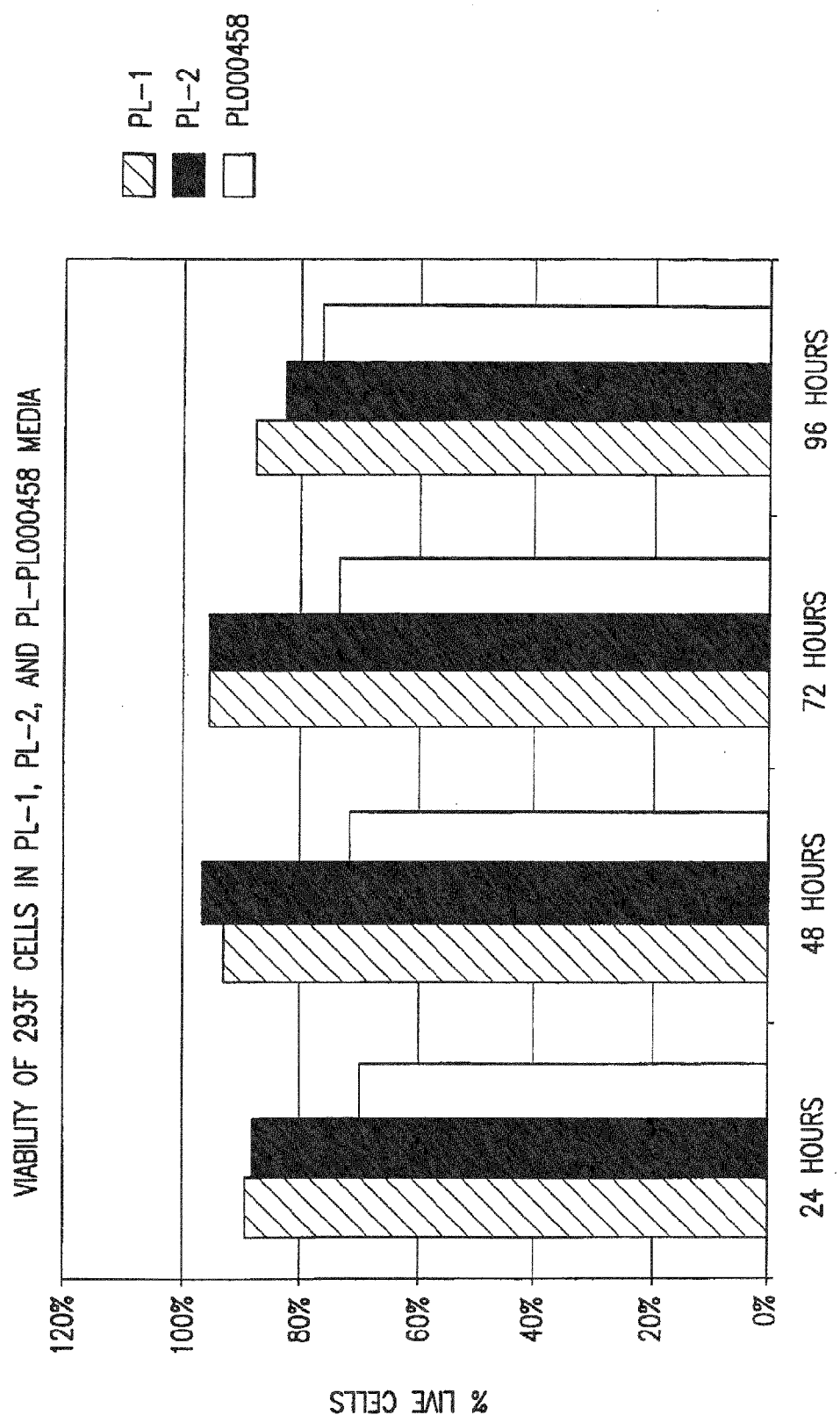

CULTURE MEDIUM FOR CELL GROWTH AND TRANSFECTION

CROSS REFERENCE TO RELATED APPLICATIONS

This application is a continuation of U.S. application Ser. No. 11/552,783, filed Oct. 25, 2006, now abandoned, which is a continuation of U.S. application Ser. No. 10/105,937, filed Mar. 26, 2002, now abandoned, which claims the benefit of Provisional Application No. 60/278,754 filed Mar. 27, 2001.

BACKGROUND OF THE INVENTION

Field of the Invention

The present invention relates to the field of cell culture. In particular, the present invention provides media suitable for the culture and transfection of cells.

Related Art

Cell culture media provide the nutrients necessary to maintain and grow cells in a controlled, artificial and in vitro environment. Characteristics and formulations of cell culture media vary depending upon the particular cellular requirements. Important parameters include osmolarity, pH, and nutrient compositions.

Cell culture medium formulations have been well documented in the literature and a large number of media are commercially available. In early cell culture work, medium formulations were based upon the chemical composition and physicochemical properties (e.g., osmolality, pH, etc.) of blood and were referred to as "physiological solutions" (Ringer, S., *J. Physiol.* 3:380-393 (1880); Waymouth, C., In: *Cells and Tissues in Culture*, Vol. 1, Academic Press, London, pp. 99-142 (1965); Waymouth, C., *In Vitro* 6:109-127 (1970)). However, cells in different tissues of a mammalian body are exposed to different microenvironments with respect to oxygen/carbon dioxide partial pressure and concentrations of nutrients, vitamins, and trace elements; accordingly, successful in vitro culture of different cell types may require the use of different medium formulations. Typical components of cell culture media include amino acids, organic and inorganic salts, vitamins, trace metals, sugars, lipids and nucleic acids, the types and amounts of which may vary depending upon the particular requirements of a given cell or tissue type.

Medium formulations have been used to cultivate a number of cell types including animal, plant and bacterial cells. Cultivated cells have many uses including the study of physiological processes and the production of useful biological substances. Examples of such useful products include monoclonal antibodies, hormones, growth factors, enzymes and the like. Such products have many commercial and therapeutic applications and, with the advent of recombinant DNA technology, cells can be engineered to produce large quantities of these products. Cultured cells are also routinely used for the isolation, identification and growth of viruses which can be used as vectors and/or vaccines. Thus, the ability to cultivate cells in vitro is not only important for the study of cell physiology, but is also necessary for the production of useful substances which may not otherwise be obtained by cost-effective means.

Among the various cell types that have been grown using in vitro cell culture media, of particular interest are cells derived from the epithelium. The epithelium lines the internal and external surfaces of the organs and glands of higher organisms. Because of this localization at the external interface between the environment and the organism (e.g., the skin) or at the internal interface between an organ and the interstitial space (e.g., the intestinal mucosal lining), the epithelium has a major role in the maintenance of homeostasis. The epithelium carries out this function, for example, by regulating transport and permeability of nutrients and wastes (Freshney, R. I., in: *Culture of Epithelial Cells*, Freshney, R. I., ed., New York: Wiley-Liss, pp. 1-23 (1992)).

The cells making up the epithelium are generically termed epithelial cells. These cells can be present in multiple layers as in the skin, or in a single layer as in the lung alveoli. As might be expected, the structure, function and physiology of epithelial cells are often tissue-specific. For example, the epidermal epithelial cells of the skin are organized as stratified squamous epithelium and are primarily involved in forming a protective barrier for the organism, while the secretory epithelial cells of many glands are often found in single layers of cuboidal cells that have a major role in producing secretory proteins and glycoproteins. Regardless of their location or function, however, epithelial cells are usually regenerative. That is, under normal conditions, or in response to injury or other activating stimulus, epithelial cells are capable of dividing or growing. This regenerative capacity has facilitated the in vitro manipulation of epithelial cells, to the point where a variety of primary epithelial cells and cell lines have been successfully cultivated in vitro (Freshney, Id.).

While the isolation and use of a variety of epithelial cells and epithelial cell lines have been reported in the literature, the human embryonic kidney cell line 293 ("293 cells"), which exhibits epithelial morphology, has proven particularly useful for studies of the expression of exogenous ligand receptors, production of viruses and expression of allogeneic and xenogeneic recombinant proteins. For example, U.S. Pat. No. 5,166,066 describes the construction of a stable 293 cell line comprising functional GABA receptors that include a benzodiazepine binding site that have proven useful in identification and screening of candidate psychoactive drugs. 293 cells have also been used to produce viruses such as natural and recombinant adenoviruses (Garnier, A., et al., *Cytotechnol.* 15:145-155 (1994); Bout, A., et al., *Cancer Gene Therapy* 3(6):S24, abs. P-52 (1996); Wang, J.-W., et al., *Cancer Gene Therapy* 3(6):S24, abs. P-53 (1996)), which can be used for vaccine production or construction of adenovirus vectors for recombinant protein expression. Finally, 293 cells have proven useful in large-scale production of a variety of recombinant human proteins (Berg, D. T., et al., *BioTechniques* 14(6):972-978 (1993); Pcshwa, M. V., et al., *Biotechnol. Bioeng.* 41:179-187 (1993); Garnier, A., et al., *Cytotechnol.* 15:145-155 (1994)).

Cells loosely called fibroblasts have been isolated from many different tissues and are understood to be connective tissue cells. It is clearly possible to cultivate cell lines, loosely termed fibroblastic cells, from embryonic and adult tissues. Fibroblasts characteristically have a "spindle" appearance. Fibroblast-like cells have morphological characteristics typical of fibroblast cells. Under a light microscope the cells appear pointed and elongated ("spindle shaped") when they grow as a monolayer on the surface of a culture vessel. Cell lines can be regarded as fibroblast or fibroblast-like after confirmation with appropriate markers, such as collagen, type I ((Freshney, R. I., in: *Culture of Epithelial Cells*, Freshney, R. I., ed., New York: Wiley-Liss, pp. 1-23 (1987)).

CHO cells have been classified as both epithelial and fibroblast cells derived from the Chinese hamster ovary. A cell line started from Chinese hamster ovary (CHO-K1)

(Kao, F.-T. And Puck, T. T., *Proc. Natl. Acad. Sci. USA* 60:1275-1281 (1968) has been in culture for many years but its identity is still not confirmed.

Most primary mammalian epithelial cells, mammalian fibroblast cells, epithelial cell lines, and fibroblast cell lines are typically grown in monolayer culture. For some applications, however, it would be advantageous to cultivate such cells as suspension cultures. For example, suspension cultures grow in a three-dimensional space. Monolayer cultures in similar-sized vessels, however, can only grow two-dimensionally on the vessel surface. Thus, suspension cultures can result in higher cell yields and, correspondingly, higher yields of biologicals (e.g., viruses, recombinant polypeptides, etc.) compared to monolayer cultures. In addition, suspension cultures are often easier to feed and scale-up, via simple addition of fresh culture media (dilution subculturing) to the culture vessel rather than trypsinization and centrifugation as is often required with monolayer cultures. The ease of feeding and the ease with which suspension cultures can be scaled up represent a substantial saving in time and labor for handling a comparable number of cells.

Many anchorage-dependent cells, such as primary epithelial cells, primary fibroblast cells, epithelial cell lines, and fibroblast cell lines, however, are not easily adapted to suspension culture. Since they are typically dependent upon anchorage to a substrate for optimal growth, growth of these cells in suspension can require their attachment to microcarriers such as latex or collagen beads. Thus, cells grown in this fashion, while capable of higher density culture than traditional monolayer cultures, are still technically attached to a surface; subculturing of these cells therefore requires similar steps as those used for the subculturing of monolayer cultures. Furthermore, when large batch or fermenter cultures are established, a large volume of microcarriers often settles to the bottom of the culture vessel, thereby requiring a more complicated agitation mechanism to keep the microcarriers (and thus, the cells) in suspension without causing shear damage to the cells (Peshwa, M. V., et al., *Biotechnol. Bioeng.* 41:179-187 (1993)).

Although many transformed cells are capable of being grown in suspension (Freshney, R. I., *Culture of Animal Cells: A Manual of Basic Technique*, New York: Alan R. Liss, Inc., pp. 123-125 (1983)), successful suspension cultures often require relatively high-protein media or supplementation of the media with serum or serum components (such as the attachment factors fibronectin and/or vitronectin), or sophisticated perfusion culture control systems (Kyung, Y.-S., et al., *Cytotechnol.* 14:183-190 (1994)), which can be disadvantageous. In addition, many epithelial cells when grown in suspension form aggregates or "clumps" which can interfere with successful subculturing and reduce growth rate and production of biologicals by the cultures. When clumping occurs, the overall cellular surface area exposed to medium is decreased and the cells are deprived of nutrition and are unable to efficiently exchange waste into the medium. As a result, growth slows, diminished cell densities are obtained, and protein expression is compromised.

Typically, cell culture media formulations are supplemented with a range of additives, including undefined components such as fetal bovine serum (FBS) (5-20% v/v) or extracts from animal embryos, organs or glands (0.5-10% v/v). While FBS is the most commonly applied supplement in animal cell culture media, other serum sources are also routinely used, including newborn calf, horse and human. Organs or glands that have been used to prepare extracts for the supplementation of culture media include submaxillary gland (Cohen, S., *J. Biol. Chem.* 237:1555-1565 (1961)), pituitary (Peehl, D. M., and Ham, R. G., *In Vitro* 16:516-525 (1980); U.S. Pat. No. 4,673,649), hypothalamus (Maciag, T., et al., *Proc. Natl. Acad. Sci. USA* 76:5674-5678 (1979); Gilchrest, B. A., et al., *J. Cell. Physiol.* 120:377-383 (1984)), ocular retina (Barretault, D., et al., *Differentiation* 18:29-42 (1981)) and brain (Maciag, T., et al., *Science* 211:1452-1454 (1981)). These types of chemically undefined supplements serve several useful functions in cell culture media (Lambert, K. J. et al., In: *Animal Cell Biotechnology*, Vol. 1, Spier, R. E. et al., Eds., Academic Press New York, pp. 85-122 (1985)). For example, these supplements provide carriers or chelators for labile or water-insoluble nutrients; bind and neutralize toxic moieties; provide hormones and growth factors, protease inhibitors and essential, often unidentified or undefined low molecular weight nutrients; and protect cells from physical stress and damage. Thus, serum or organ/gland extracts are commonly used as relatively low-cost supplements to provide an optimal culture medium for the cultivation of animal cells.

Unfortunately, the use of serum or organ/gland extracts in tissue culture applications has several drawbacks (Lambert, K. J. et al., In: *Animal Cell Biotechnology*, Vol. 1, Spier, R. E. et al., Eds., Academic Press New York, pp. 85-122 (1985)). For example, the chemical compositions of these supplements and sera vary between lots, even from a single manufacturer. The supplements can also be contaminated with infectious agents (e.g., mycoplasma and viruses) which can seriously undermine the health of the cultured cells and the quality of the final product. The use of undefined components such as serum or animal extracts also prevents the true definition and elucidation of the nutritional and hormonal requirements of the cultured cells, thus eliminating the ability to study, in a controlled way, the effect of specific growth factors or nutrients on cell growth and differentiation in culture. Moreover, undefined supplements prevent the researcher from studying aberrant growth and differentiation and the disease-related changes in cultured cells. Finally and most importantly to those employing cell culture media in the industrial production of biological substances, serum and organ/gland extract supplementation of culture media can complicate and increase the costs of the purification of the desired substances from the culture media due to nonspecific co-purification of serum or extract proteins.

Improved levels of recombinant protein expression are obtained from cells grown in serum-free medium, relative to the level of expression seen in cells grown in medium supplemented with serum (Battista, P. J. et al., *Am. Biotech. Lab.* 12:64-68 (1994)). However, serum-free media can still contain one or more of a variety of animal-derived components, including albumin, fetuin, various hormones and other proteins. The presence of proteins or peptides makes purification of recombinant protein difficult, time-consuming, and expensive.

To overcome these drawbacks of the use of serum or organ/gland extracts, a number of so-called "defined" media have been developed. These media, which often are specifically formulated to support the culture of a single cell type, contain no undefined supplements and instead incorporate defined quantities of purified growth factors, proteins, lipoproteins and other substances usually provided by the serum or extract supplement. Since the components (and concentrations thereof) in such culture media are precisely known, these media are generally referred to as "defined culture media." Sometimes used interchangeably with "defined culture media" is the term "serum-free media" or "SFM." A number of SFM formulations are commercially available, such as those designed to support the culture of endothelial cells, keratinocytes, monocytes/macrophages, lymphocytes, hematopoietic stem cells, fibroblasts, chondrocytes or hepatocytes which are available from Invitrogen Corporation, Carlsbad, Calif. The distinction between SFM and defined media, however, is that SFM are media devoid of serum and protein fractions (e.g., serum albumin), but not necessarily of other undefined components such as organ/gland extracts. Indeed, several SFM that have been reported or that are available commercially contain such undefined components, including several formulations supporting in vitro culture of keratinocytes (Boyce, S. T., and Ham, R. G., *J. Invest. Dermatol.* 81:33 (1983); Wille, J. J., et al., *J. Cell. Physiol.* 121:31 (1984); Pittelkow, M. R., and Scott, R. E., *Mayo Clin. Proc.* 61:771 (1986); Pirisi, L., et al., *J. Virol.* 61:1061 (1987); Shipley, G. D., and Pittelkow, M. R., *Arch. Dermatol.* 123:1541 (1987); Shipley, G. D., et al., *J. Cell. Physiol.* 138:511-518 (1989); Daley, J. P., et al., *FOCUS (GIBCO/LTI)* 12:68 (1990); U.S. Pat. Nos. 4,673,649 and 4,940,666). SFM thus cannot be considered to be defined media in the true definition of the term.

Defined media generally provide several distinct advantages to the user. For example, the use of defined media facilitates the investigation of the effects of a specific growth factor or other medium component on cellular physiology, which can be masked when the cells are cultivated in serum- or extract-containing media. In addition, defined media typically contain much lower quantities of protein (indeed, defined media are often termed "low protein media") than those containing serum or extracts, rendering purification of biological substances produced by cells cultured in defined media far simpler and less expensive.

Some extremely simple defined media, which consist essentially of vitamins, amino acids, organic and inorganic salts and buffers have been used for cell culture. Such media (often called "basal media"), however, are usually seriously deficient in the nutritional content required by most animal cells. Accordingly, most defined media incorporate into the basal media additional components to make the media more nutritionally complex, but to maintain the serum-free and low protein content of the media. Examples of such components include bovine serum albumin (BSA) or human serum albumin (HSA); certain growth factors derived from natural (animal) or recombinant sources such as epidermal growth factor (EGF) or fibroblast growth factor (FGF); lipids such as fatty acids, sterols and phospholipids; lipid derivatives and complexes such as phosphoethanolamine, ethanolamine and lipoproteins; protein and steroid hormones such as insulin, hydrocortisone and progesterone; nucleotide precursors; and certain trace elements (reviewed by Waymouth, C., in: *Cell Culture Methods for Molecular and Cell Biology, Vol. 1: Methods for Preparation of Media, Supplements, and Substrata for Serum-Free Animal Cell Culture*, Barnes, D. W., et al., eds., New York: Alan R. Liss, Inc., pp. 23-68 (1984), and by Gospodarowicz, D., Id., at pp 69-86 (1984)).

The use of animal protein supplements in cell culture media, however, also has certain drawbacks. For example, there is a risk that the culture medium and/or products purified from it can be immunogenic, particularly if the supplements are derived from an animal different from the source of the cells to be cultured. If biological substances to be used as therapeutics are purified from such culture media, certain amounts of these immunogenic proteins or peptides can be co-purified and can induce an immunological reaction, up to and including anaphylaxis, in an animal receiving such therapeutics.

To obviate this potential problem, supplements derived from the same species as the cells to be cultured can be used. For example, culture of human cells can be facilitated using HSA as a supplement, while media for the culture of bovine cells would instead use BSA. This approach, however, runs the risks of introducing contaminants and adventitious pathogens into the culture medium (such as Creutzfeld-Jakob Disease (CJD) from HSA preparations, or Bovine Spongiform Encephalopathy ("Mad Cow Disease") prion from BSA preparations), which can obviously negatively impact the use of such media in the preparation of animal and human therapeutics. In fact, for such safety reasons, the biotechnology industry and government agencies are increasingly regulating, discouraging and even forbidding the use of cell culture media containing animal-derived proteins which can contain such pathogens.

To overcome the limitations of the use of animal proteins in SFM, several attempts have been made to construct animal cell culture media that are completely free of animal proteins. For example, some culture media have incorporated extracts of yeast cells into the basal medium (see, for example, U.K. Patent Application No. GB 901673; Keay, L., *Biotechnol. Bioengin.* 17:745-764 (1975)) to provide sources of nitrogen and other essential nutrients. In another approach, hydrolysates of wheat gluten have been used, with or without addition of yeast extract, to promote in vitro growth of animal cells (Japanese Patent Application No. JP 2-49579). Still other media have been developed in which serum is replaced by enzymatic digests of meat, or of proteins such as α-lactalbumin or casein (e.g., peptone), which have been traditionally used in bacterial culture (Lasfargues, E. Y., et al., *In Vitro* 8(6):494-500 (1973); Keay, L., *Biotechnol. Bioeng.* 17:745-764 (1975); Keay, L., *Biotechnol. Bioeng.* 19:399-411 (1977); Schlager, E.-J., *J. Immunol. Meth.* 194:191-199 (1996)). None of these approaches, however, provided a culture medium optimal for the cultivation of a variety of animal cells. Moreover, extracts from certain plants, including wheat, barley, rye and oats have been shown to inhibit protein synthesis in cell-free systems derived from animal cells (Coleman, W. H., and Roberts, W. K., *Biochim. Biophys. Acta* 696:239-244 (1982)), suggesting that the use of peptides derived from these plants in cell culture media can actually inhibit, rather than stimulate, the growth of animal cells in vitro. More recently, animal cell culture SFM formulations comprising rice peptides have been described and shown to be useful in cultivation of a variety of normal and transformed animal cells (see U.S. Pat. No. 6,103,529, incorporated herein by reference in its entirety).

Notwithstanding the potential difficulties posed by the addition of animal derived supplements to cell culture media, such supplements are in routine use. One such supplement that is frequently added to defined media is transferrin. Transferrin functions in vivo to deliver iron to cells. The mechanism of iron uptake by mammalian cells has been reviewed (Qian, Z. M. and Tang, P. L. (1995) *Biochim. Biophys. Acta* 1269, 205-214). As iron is required as a co-factor in numerous metabolic processes including energy generation and oxidative respiration, serum-free media are often supplemented with transferrin in order to deliver the requisite iron for the successful cultivation of most cells in vitro. Concern about various potential adventitious agents in preparations of transferrin has stimulated a search for other natural iron carrier compounds which can be used as a substitute for transferrin. This search is complicated by the fact that the natural iron carriers are often derived from serum and thus are subject to the above-described limitations of serum supplementation.

To overcome the limitations of using naturally derived metal carriers, certain metal binding compounds are being explored for use in supplying metals, particularly zinc, iron, manganese and magnesium, to cultured cells. Simple carriers such as chelating agents (e.g., EDTA) and certain acids or salts thereof (e.g., citrate, picolinate, and derivatives of benzoic acid or hydroxamic acid) have been shown to be useful in certain serum-free growth media (see U.S. Pat. Nos. 5,045,454 and 5,118,513; Testa et al., *Brit. J. Haematol.* 60:491-502, (1985); Ganeshaguru et al., *Biochem. Pharinacol.* 29:1275-1279 (1980); White et al., *Blood* 48:923-929 (1976)).

Although these references disclose some metal carriers, the interpretation of the data is complicated by several experimental factors. The data were gathered from a limited number of cell lines and show results of a single passage. In addition, the media were supplemented with serum. Serum inherently contains transferrin and other potential iron carriers. There is a "carry-over effect" on growth of cells which have been cultured in serum-supplemented medium, even after one or two passages in the absence of serum or transferrin (see, for example, Keenan, J. and Clynes, M. (1996) In Vitro Cell Dev. Biol-Animal 32, 451-453). Other known metal binding compounds have been used medicinally to remove iron from the body and not for delivery. Unfortunately, many of these simple iron chelating compounds do not provide sufficient iron availability to, or uptake by, cultured cells.

Once a suitable medium formulation for the growth of a particular cell type has been determined, it is frequently necessary to alter the cell in question so as to optimize the production of a desired biological substance. A critical step in the effective production and purification of biological substances is the introduction of one or more macromolecules (e.g., peptides, proteins, nucleic acids, etc.) into the cell in which the material will be produced. This can be accomplished by a variety of methods. One widely used method to introduce macromolecules into a cell is known as transfection.

Typically, the target cell is grown to a desired cell density in a cell culture medium optimized for growth of the cell. Once the desired density is reached, the medium is exchanged for a medium optimized for the transfection process. Under most circumstances, the medium used for transfection does not support the growth of the cells but the transfection medium is merely used for the purpose of introducing nucleic acids into the cells. As a result, the process generally requires collecting the cells from the culture, usually by centrifugation, washing the cells to remove traces of the growth medium, suspending the cells in a transfection medium in the presence of the macromolecule of interest, incubating the cells in the transfection medium for a period of time sufficient for the uptake of the macromolecule, optionally, removing the transfection medium and washing the remnants of the transfection medium from the cells and then re-suspending the transfected cells in a growth medium. The steps of exchanging the growth media for transfection media, washing the cells, and exchanging the transfection media back to a growth media require a great deal of hands-on manipulation of the cells thereby adding substantially to the time and expense of recombinant DNA technology.

As an historical example, 293 cells have been cultivated in monolayer cultures in a serum-supplemented version of a complex medium (i.e., DMEM). When grown in suspension, 293 cells have a tendency to aggregate into large clusters of cells. The formation of these large cell aggregates reduces the viability of the cells. Since the cells in the center of the aggregates are not directly exposed to the medium, these cells have limited access to nutrients in the medium and have difficulty in exchanging waste into the medium. In addition, this reduced access to the medium makes cells in clusters unsuitable for genetic manipulation by factors introduced into the medium (i.e., for transformation by nucleic acids). As a result of these difficulties, 293 cells have not generally been used in suspension culture for the production of biological materials.

Thus, there still remains a need in the art for a cell medium that permits the growth of eukaryotic cells in suspension while permitting the transfection of the cells with a reduced amount of manipulation. Such a medium should preferably be a serum-free and/or chemically defined and/or protein-free medium and/or a medium lacking animal derived materials which facilitates the growth of mammalian cells to high density and/or increases the level of expression of recombinant protein, reduces cell clumping, and which does not require supplementation with animal proteins, such as serum, transferrin, insulin and the like. Preferably a medium of this type will permit the suspension cultivation of mammalian cells that are normally anchorage-dependent, including epithelial cells and fibroblast cells, such as 293 cells and CHO cells. Such culture media will facilitate studies of the effects of growth factors and other stimuli on cellular physiology, will allow easier and more cost-effective production and purification of biological substances (e.g., viruses, recombinant proteins, etc.) produced by cultured mammalian cells in the biotechnology industry, and will provide more consistent results in methods employing the cultivation of mammalian cells. These needs and others are met by the present invention.

SUMMARY OF THE INVENTION

The present invention provides a cell culture medium, wherein the medium supports introduction of one or more macromolecules into at least one eukaryotic cell in culture and supports cultivation of the at least one cell subsequent to the introduction, wherein growth of the at least one cell continues in the medium in the absence of the medium being with fresh medium. In a preferred embodiment, it is not necessary to remove medium used during the introduction from the presence of the at least one cell to support growth of the at least one cell. In another preferred embodiment, after the introduction, growth is accomplished in cultivation in a volume of medium that is about the same volume up to no more than about 10 times the volume of the medium in which the introduction occurred. Using the medium of the present invention, it is not necessary to replenish, replace or supplement the medium after one has introduced nucleic acid into cells, and before cells into which nucleic acid has been introduced are further cultured to express the nucleic acid.

The present invention also provides a method of making a medium comprising admixing water and at least one ingredient selected from the group consisting of an amino acid, a sugar, a fatty acid (such as linoleic acid, linolenic acid, and especially fatty acids of 12, 14, 16, 18, 19, 20 or 24 carbon atoms, each carbon chain branched or unbranched), arachadonic acid, palmitoleic acid, oleic acid, polyenoic acid (e.g., palmitoleic acid, oleic acid, linoleic acid and/or linolenic acid), a vitamin (such as pyridoxine, niacinamide, thiamine, etc.), a pH buffer, a surfactant, a trace metal or salt or hydrate thereof, an amine compound, a growth factor, an agent to control osmolarity and/or ionic strength and/or maintain membrane potential, a flavin, a compound that participates in or is a product of the glycolytic pathway, an alcoholamine, a cyclic alcohol, a phospholipid or portion thereof (such as choline chloride), a salt of selenious acid (such as sodium selenite), a divalent or trivalent cation (such as manganese, calcium, zinc, magnesium, copper or iron), a pteridine derivative (such as folic acid), a valeric acid (such as lipoic acid) and/or a coenzyme (such as riboflavin), wherein the medium supports (a) the introduction of at least one macromolecule into eukaryotic cells in culture, (b) the cultivation of cells into which at least one macromolecule is introduced, and optionally (c) the expression of a nucleic acid in cells into which a macromolecule is introduced to form a protein product, wherein medium containing the at least one molecule does not need to be removed from the culture and replaced with fresh medium after introduction of the at least one molecule into cells and prior to cultivation and optimal expression of the nucleic acid.

The present invention also provides the medium obtained by admixing water and at least one ingredient selected from the group consisting of an amino acid, a sugar, a fatty acid (such as linoleic acid, linolenic acid, and especially fatty acids of 12, 14, 16, 18, 19, 20 or 24 carbon atoms, each carbon chain branched or unbranched), arachadonic acid, palmitoleic acid, oleic acid, polyenoic acid (e.g., palmitoleic acid, oleic acid, linoleic acid and/or linolenic acid), a vitamin (such as pyridoxine, niacinamide, thiamine, etc.), a pH buffer, a surfactant, a trace metal or salt or hydrate thereof, an amine compound, a growth factor, an agent to control osmolarity and/or ionic strength and/or maintain membrane potential, a flavin, a compound that participates in or is a product of the glycolytic pathway, an alcoholamine, a cyclic alcohol, a phospholipid or portion thereof (such as choline chloride), a salt of selenious acid (such as sodium selenite), a divalent or trivalent cation (such as manganese, calcium, zinc, magnesium, copper or iron), a pteridine derivative (such as folic acid), a valeric acid (such as lipoic acid) and/or a coenzyme (such as riboflavin), wherein the medium supports (a) the introduction at least one macromolecule into at least one eukaryotic cell in culture, (b) the cultivation of at least one cell into which at least one macromolecule is introduced, and (c) the expression of a nucleic acid in cells into which a macromolecule is introduced, wherein medium containing the at least one macromolecule does not need to be removed from the culture and replaced with fresh medium after introduction of the at least one macromolecule into cells and prior to cultivation and optimal expression of the nucleic acid.

The present invention also provides a method of cultivating eukaryotic cells comprising: (a) contacting the cells with the cell culture medium of the present invention; (b) maintaining the cells under conditions suitable to support cultivation of the cells in culture; and (c) optionally expressing a nucleic acid to form a protein product.

The present invention also provides a method for introducing one or more macromolecules into at least one eukaryotic cell in culture, the method comprising: (a) culturing at least one eukaryotic cell in the medium of claim 1 in culture; (b) introducing at least one macromolecule into the culture under conditions sufficient to cause one or more of the at least one macromolecule to be introduced in the at least one cell; and (c) cultivating the at least one cell in the medium to produce a product whose production is controlled by the at least one molecule, wherein growth of the at least one cell continues in the medium in the absence of the medium being with fresh medium, wherein it is not necessary to remove medium used during the introduction from the presence of the at least one cell to support growth of the at least one cell, and/or wherein after the introduction, growth is accomplished in cultivation in a volume of medium that is about the same volume up to no more than about 10 times the volume of the medium in which the introduction occurred.

The present invention also provides a kit for the cultivation and transfection of cells in vitro, the kit comprising the cell culture medium of the present invention, and optionally further comprising one or more of: one or more agents for the introduction of at least one molecule into a cell, one or more macromolecules, at least one cell, and instructions for culturing the at least one cell in culture and/or for introducing at least one macromolecule into at least one cell in culture.

The present invention also provides a composition comprising the cell culture medium of the present invention and at least one component selected from the group consisting of at least one eukaryotic cell, one or more agents for the introduction of at least one macromolecule into at least one cell, and one or more macromolecules.

Other embodiments of the present invention will be apparent to one of ordinary skill in light of the following drawings and description of the invention, and of the claims.

BRIEF DESCRIPTION OF THE DRAWINGS/FIGURES

Figure 1B:
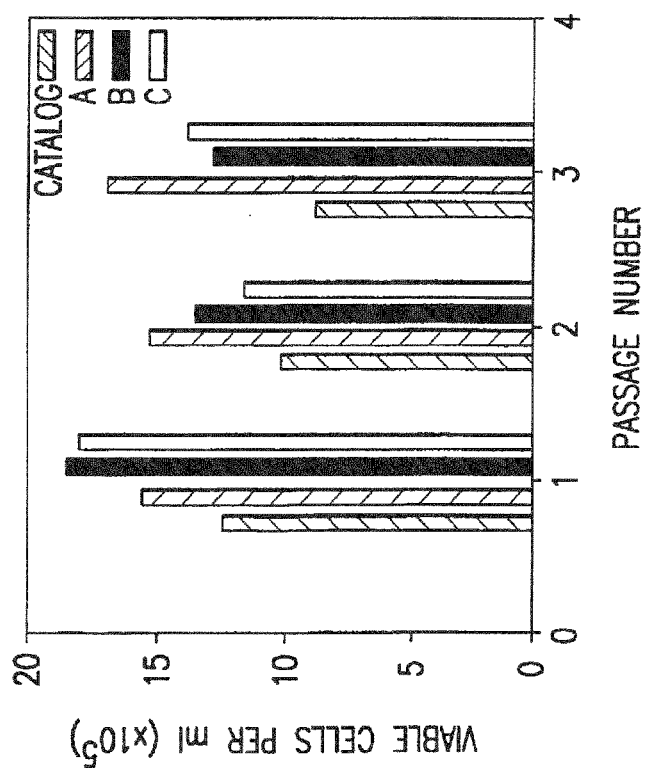

FIG. 1A is a bar graph showing a plot of the number of 293-F cells/ml as a function of passage number in the medium of the present invention. FIG. 1B is a bar graph showing a plot of the number of 293-H cells/ml as a function of passage number in the medium of the present invention. Growth for 293-F and 293-H cells cultured in 293 SFM II medium (Invitrogen Corp., Carlsbad, Calif.) vs. prototype media A, B and C. 15 ml cultures were seeded at $3\times10^5$ viable cells per ml in 125 ml shaker flasks in the media one passage after recovery from cryopreservation. Cells were counted and split every four days to $3\times10^5$ viable cells per ml. At passage 3, cells were used to seed cultures for a growth curve. In FIG. 1A, at each passage number, the respective bars correspond, from left to right, to 293 SFM II medium, medium A, medium B, and medium C. In FIG. 1B, at each passage number, the respective bars correspond, from left to right, to 293 SFM II medium, and medium A.

Figure 2B:
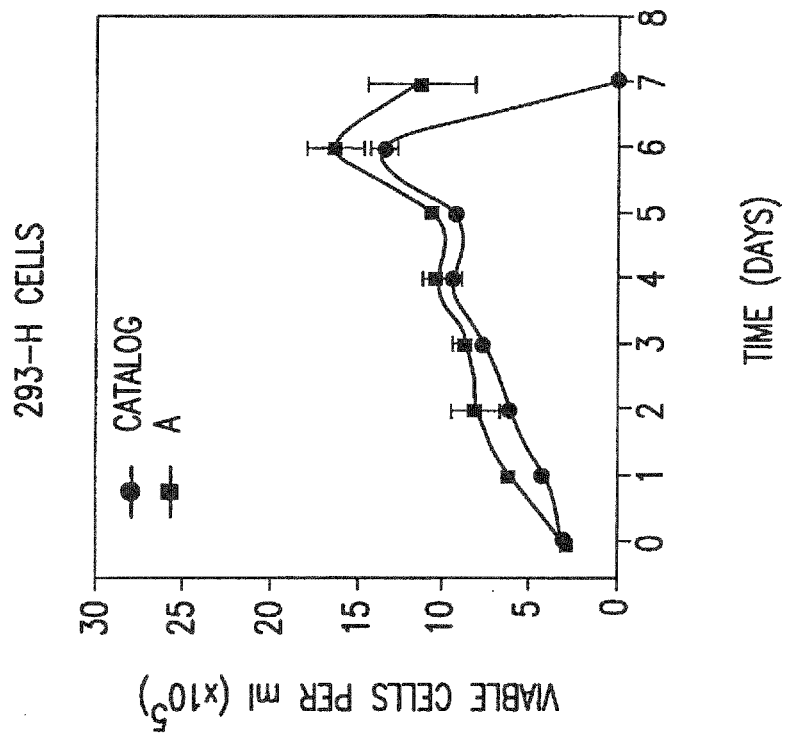
Figure 2A:
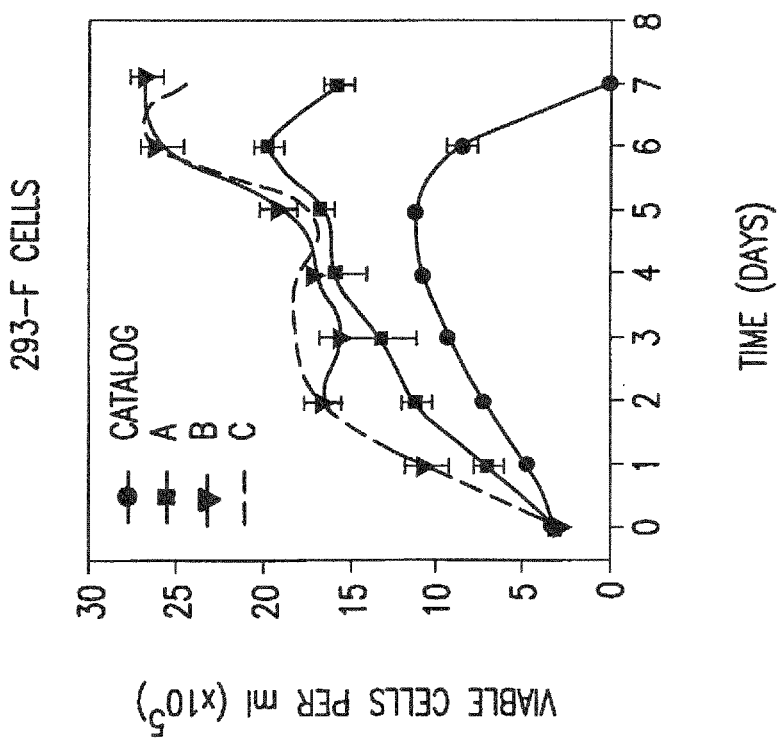

FIG. 2A is a graph showing the number of viable 293-F cells/ml as a function of the number of days cultured in the medium of the invention. FIG. 2B is a graph showing the number of viable 293-H cells/ml as a function of the number of days cultured in the medium of the invention. Growth for 293-F and 293-H cells cultured in 293 SFM II medium (Invitrogen Corp., Carlsbad, Calif.) vs. prototype media A, B and C. 15 ml cultures were seeded at $3\times10^5$ viable cells per ml in 125 ml shaker flasks in triplicate and 1 ml samples taken each day for viabilities and counts. Cells were cultured in 293 SFM II medium supplemented with 4 mM L-Glutamine or in one of the tested media A, B or C.

Figure 3:
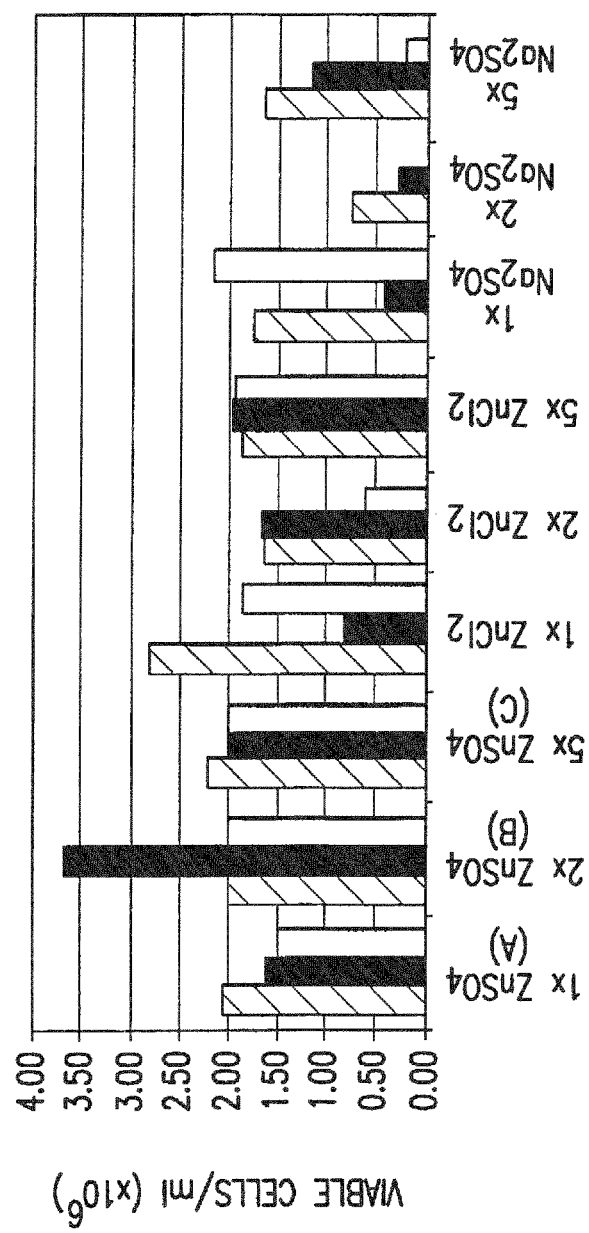

FIG. 3 is a bar graph showing a plot of the number of 293-F cells/ml after each of three passages in the medium of the invention supplemented with various salts. For each medium, the three bars correspond, from left to right, to passage 1 (p1), passage 2, (p2) and passage 3 (p3).

Figure 4A:
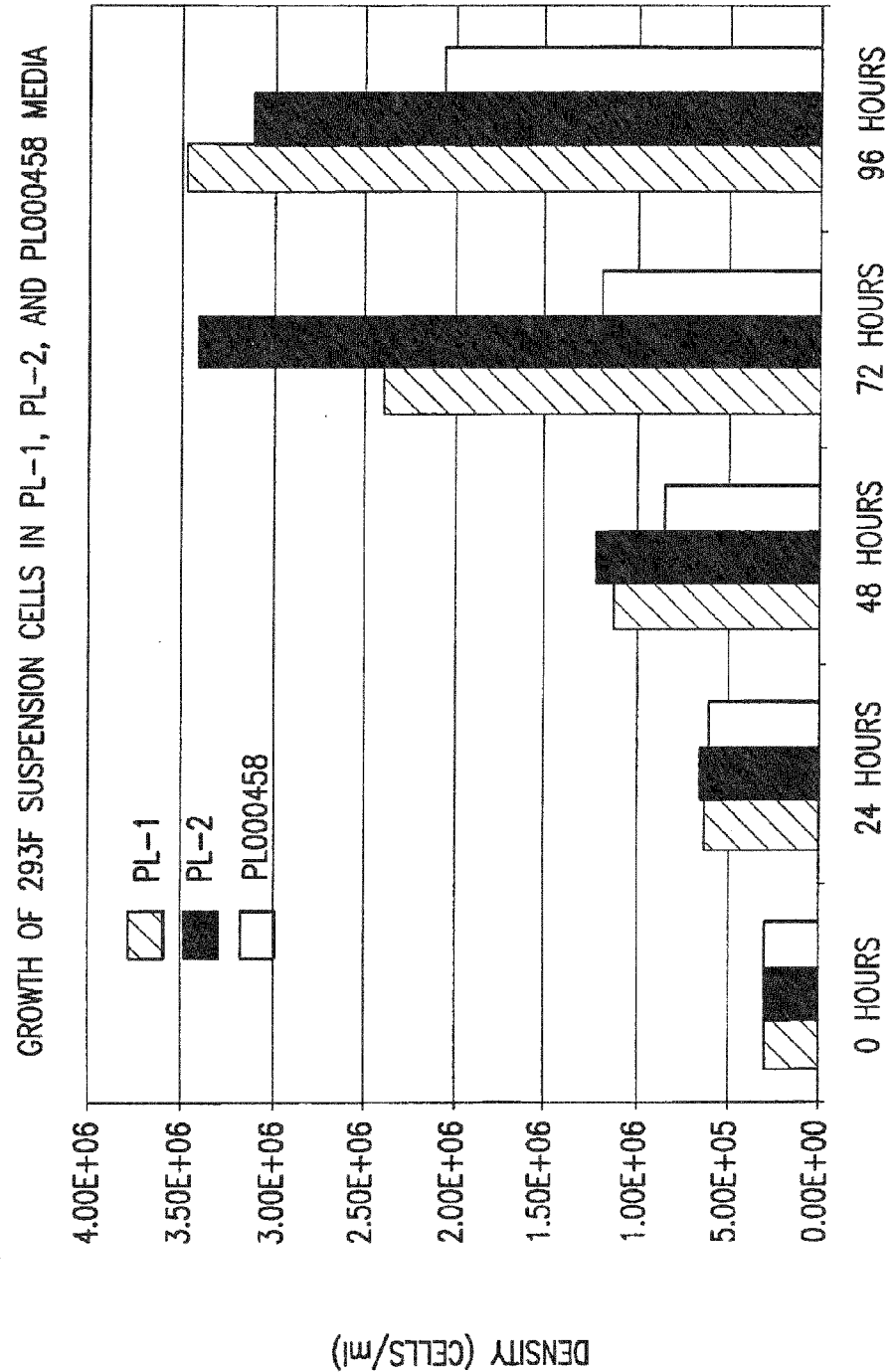
Figure 4C:
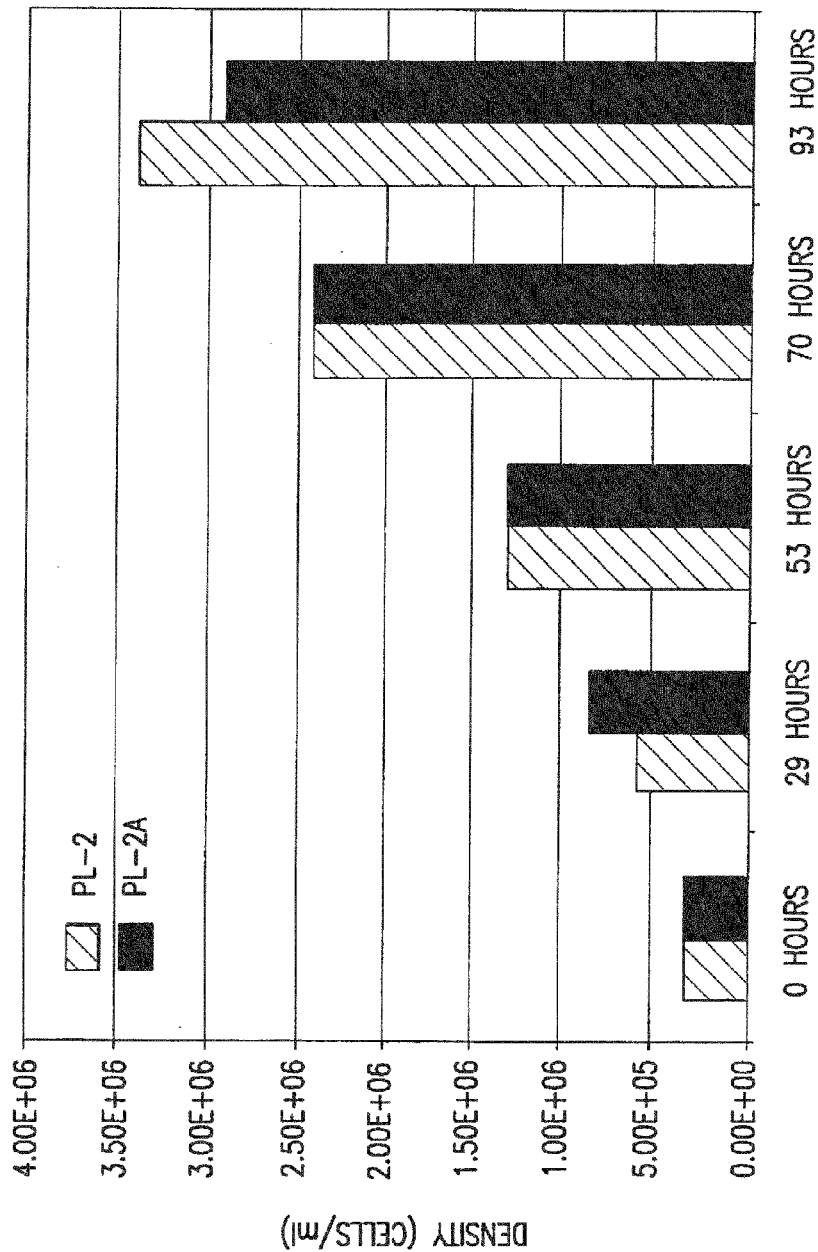
Figure 4D:
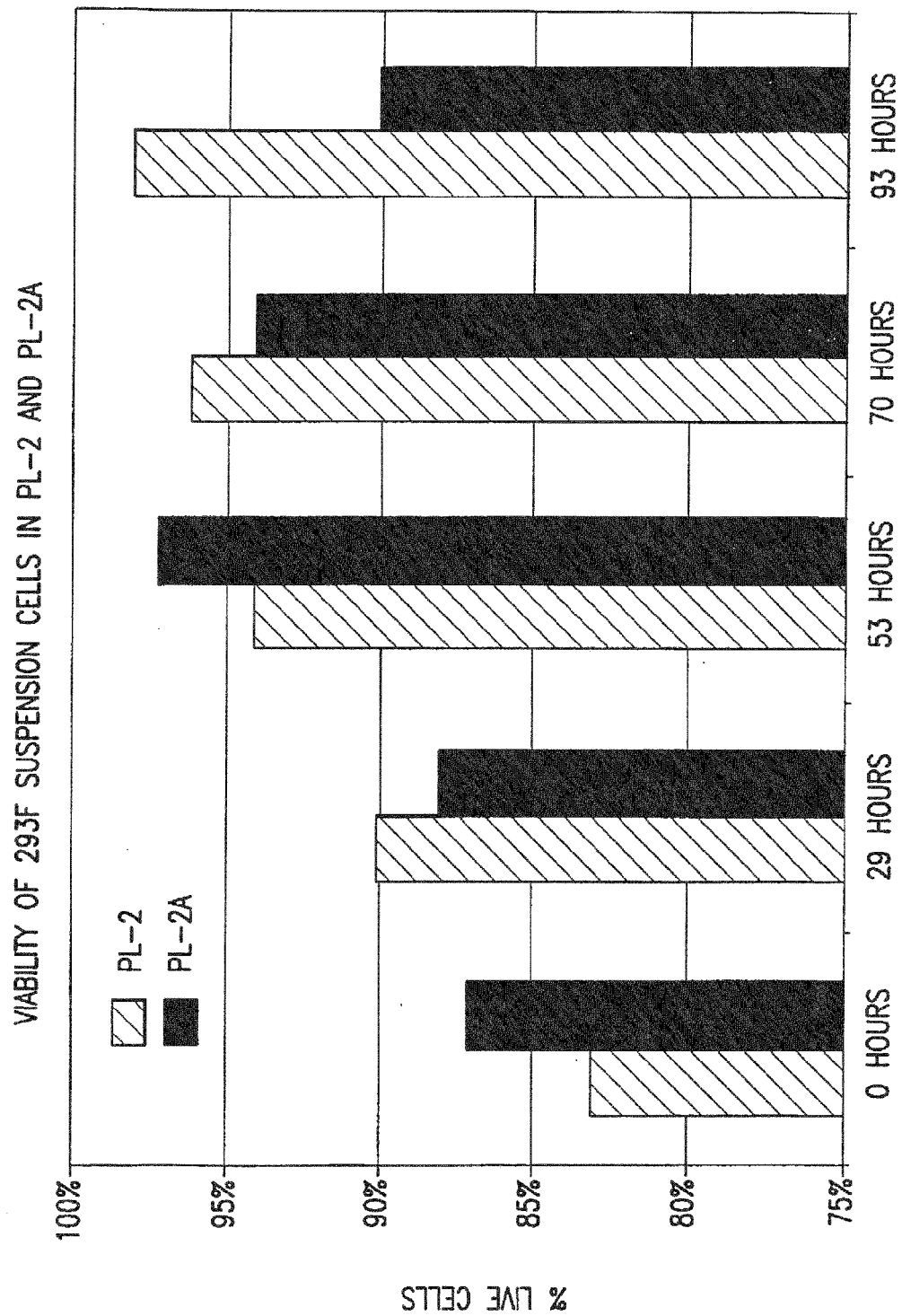

FIG. 4A is a bar graph showing a plot of 293-F cell density (cells/ml) in pilot lot 1 (PL1), pilot lot 2 (PL2) and pilot lot (PL) 000458 media. FIG. 4B is a bar graph showing a plot of % viable 293-F cells in PL1, PL-2 and PL000458 media. FIG. 4C is a bar graph showing a plot of 293-F cell density (cells/ml) in PL-2 and PL-2A (+insulin) media. FIG. 4D is a bar graph showing a plot of % viable 293-F cells in PL-2 and PL-2A (+insulin) media.

DETAILED DESCRIPTION OF THE INVENTION

The present invention provides improved medium formulations for the growth of both eukaryotic and prokaryotic cells. The inventive media support cell growth, introduction of macromolecules into cells in culture and cell cultivation without requiring replenishment, replacement, supplementation, or changing medium between growth, introduction and/or cultivation. The media of the present invention can be used to support or enhance the growth and cultivation of any cell. The present invention also provides compounds that can be used as substitutes or to replace one or more undesired components, e.g., animal derived components. The replacement compounds provide at least one desired function of the undesired component.

Definitions

In the description that follows, a number of terms used in cell culture and recombinant DNA technology are utilized extensively. In order to provide a clear and more consistent understanding of the specification and claims, including the scope to be given such terms, the following definitions are provided.

The term "introduction" of a macromolecule or compound into culture refers to the provision of the macromolecule or compound into the culture medium.

The term "introduction" of a macromolecule or compound into at least one cell refers to the provision of a macromolecule or compound to a cell, such that the macromolecule or compound becomes internalized in the cell. For example, a macromolecule or compound can be introduced into a cell using transfection, transformation, injection, and/or liposomal introduction, and may also be introduced into a cell using other methods known to those of ordinary skill in the art. Preferably, a macromolecule or compound is introduced into a cell by liposomal introduction. The macromolecule is preferably a protein, peptide, polypeptide, or nucleic acid. The macromolecule may a protein. Alternatively, the macromolecule may be a peptide. Alternatively, the macromolecule may be a polypeptide. The macromolecule may also be a nucleic acid.

The term "macromolecule," as used herein, encompasses biomolecules. In one embodiment, the term macromolecule refers to nucleic acid. In a preferred embodiment, the term macromolecule refers to deoxyribonucleic acid (DNA) and ribonucleic acid (RNA). More preferably, the term macromolecule refers to DNA. More preferably, the term macromolecule refers to complementary DNA (cDNA). A macromolecule can be charged or uncharged. A DNA molecule is an example of a charged macromolecule.

The term "nucleic acid" as used herein refers to any nucleic acid, including deoxyribonucleic acid (DNA) and ribonucleic acid (RNA). In preferred embodiments, "nucleic acid" refers to DNA, including genomic DNA, complementary DNA (cDNA), and oligonucleotides, including oligoDNA. More preferably, "nucleic acid" refers to genomic DNA and/or cDNA.

The term "expression of nucleic acid," as used herein, refers to the replication of the nucleic acid in a cell, to transcription of DNA to messenger RNA, to translation of RNA to protein, to post-translational modification of protein, and/or to protein trafficking in the cell, or variations or combinations thereof.

The term "ingredient" refers to any compound, whether of chemical or biological origin, that can be used in cell culture media to maintain or promote the growth or proliferation of cells. The terms "component," "nutrient" and "ingredient" can be used interchangeably and are all meant to refer to such compounds. Typical ingredients that are used in cell culture media include amino acids, salts, metals, sugars, lipids, nucleic acids, hormones, vitamins, fatty acids, proteins and the like. Other ingredients that promote or maintain cultivation of cells ex vivo can be selected by those of skill in the art, in accordance with the particular need. Media of the present invention can include one or more components selected from the group consisting of bovine serum albumin (BSA) or human serum albumin (HSA), a one or more growth factors derived from natural (animal) or recombinant sources such as epidermal growth factor (EGF) or fibroblast growth factor (FGF), one or more lipids, such as fatty acids, sterols and phospholipids, one or more lipid derivatives and complexes, such as phosphoethanolamine, ethanolamine and lipoproteins, one or more proteins, one or more and teroid hormones, such as insulin, hydrocortisone and progesterone, one or more nucleotide precursors; and one or more trace elements.

The term "cell" as used herein refers includes all types of eukaryotic and prokaryotic cells. In preferred embodiments, the term refers to eukaryotic cells, especially mammalian cells.

By "cell culture" or "culture" is meant the maintenance of cells in an artificial, in vitro environment.

By "cultivation" is meant the maintenance of cells in vitro under conditions favoring growth and/or differentiation and/or or continued viability. "Cultivation" can be used interchangeably with "cell culture." Cultivation is assessed by number of viable cells/ml culture medium. Cultivation after introduction of a macromolecule preferably includes production of a product, for example, a protein product on a virus.

The term "replenishing, replacing, or supplementing medium" as used herein refers to adding a volume of fresh cell culture medium to medium that was already present in culture and/or replacing medium that was already present in culture with fresh medium, and/or supplementing medium already present in culture with new medium. Fresh medium is medium that does not contain the one or more macromolecules or compounds to be introduced into at least one cell or medium that has not been in contact with cells to support their growth on cultivation. The skilled artisan can determine whether there is an advantage from or a need to remove and/or replenish, replace or supplement medium by monitoring cell growth and/or viability by techniques known in the art, such as cell counting (manual or automated), trypan blue exclusion, production of protein or other substance, alamar blue assay, presence or concentration of one or more metabolic products, cell adhesion, morphological appearance, analysis of spent medium, etc. One or a combination of monitoring techniques can be used to determine whether the medium needs to be to support growth, introduction of at least one macromolecule and/or cultivation after introduction of at least one macromolecule.

"Recombinant protein" refers to protein that is encoded by a nucleic acid that is introduced into a host cell. The host cell expresses the nucleic acid. The term "expressing a nucleic acid" is synonymous with "expressing a protein of an RNA encoded by a nucleic acid." "Protein" as used herein broadly refers to polymerized amino acids, e.g., peptides, polypeptides, proteins, lipoproteins, glycoproteins, etc.

The term "protein yield" refers to the amount of protein expressed by cultured cells, and can be measured, for example, in terms of grams of protein produced/ml medium. If the protein is not secreted by the cells, the protein can be isolated from the interior of the cells by methods known to those of ordinary skill in the art. If the protein is secreted by the cells, the protein can be isolated from the culture medium by methods known to those of ordinary skill in the art. The amount of protein expressed by the cell can readily be determined by those of ordinary skill in the art. The protein may be a recombinant protein.

A "protein product" is a product associated with production or an action by a protein. A protein product may be a protein. A protein product may also be a product resulting from action of a protein by one or more other substances to produce a product. An example of such action is enzymatic action by a protein.

By "suspension culture" is meant cell culture in which the majority or all of cells in a culture vessel are present in suspension, and the minority or none of the cells in the culture vessel are attached to the vessel surface or to another surface within the vessel. Preferably, "suspension culture" has greater than 75% of the cells in the culture vessel are in suspension, not attached to a surface on or in the culture vessel. More preferably, a "suspension culture" has greater than 85% of the cells in the culture vessel are present in suspension, not attached to a surface on or in the culture vessel. Even more preferred is a "suspension culture" with greater than 95% of the cells in the culture vessel present in suspension, not attached to a surface on or in the culture vessel.

The medium, methods, kit and composition of the present invention are suitable for either monolayer or suspension culture, transfection, and cultivation of cells, and for expression of protein in cells in monolayer or suspension culture. Preferably, the medium, methods, kit and composition of the present invention are for suspension culture, transfection, and cultivation of cells, and for expression of protein product in cells in suspension culture.

By "culture vessel" is meant any container, for example, a glass, plastic, or metal container, that can provide an aseptic environment for culturing cells.

The phrases "cell culture medium," "tissue culture medium," "culture medium" (plural "media" in each case) and "medium formulation" refer to a nutritive solution for cultivating cells or tissues. These phrases can be used interchangeably.

The term "combining" refers to the mixing or admixing of ingredients.

Derivative of a molecule includes these compounds that comprise the base cyclic or heterocyclic molecule, but have additional or modified side groups. Preferably a "derivative" can be formed by reacting the base molecule with only 1, but possibly 2, 3, 4, 5, 6, etc. reactant molecules. A single step reaction is preferred, but multi-step, e.g., 2, 3, 4, 5, 6, etc. reactions are known in the art to form derivatives. Substitution, condensation and hydrolysis reactions are preferred and may be combined to form the derivative compound. Alternatively, a derivative compound may be a compound that preferably in 1, but possibly 2, 3, 4, 5, 6, etc. reactions can form the base cyclic or heterocyclic compound or a substitution or condensation product thereto.

A cell culture medium is composed of a number of ingredients and these ingredients can vary from medium to medium. Each ingredient used in a cell culture medium has its unique physical and chemical characteristics. Compatibility and stability of ingredients are determined in part by the "solubility" of the ingredients in aqueous solution. The terms "solubility" and "soluble" refer to the ability of an ingredient to form and remain in solution with other ingredients. Ingredients are thus compatible if they can be maintained in solution without forming a measurable or detectable precipitate.

By "compatible ingredients" is also meant those media components which can be maintained together in solution and form a "stable" combination. A solution containing "compatible ingredients" is said to be "stable" when the ingredients do not precipitate, degrade or decompose substantially such that the concentration of one or more of the components available to the cells from the media is reduced to a level that no longer supports the optimum or desired growth of the cells. Ingredients are also considered "stable" if degradation cannot be detected or when degradation occurs at a slower rate when compared to decomposition of the same ingredient in a 1× cell culture media formulation. For example, in 1× media formulations glutamine is known to degrade into pyrolidone carboxylic acid and ammonia. Glutamine in combination with divalent cations are considered "compatible ingredients" since little or no decomposition of the glutamine can be detected over time in solutions or combinations in which both glutamine and divalent cations are present. See U.S. Pat. No. 5,474,931. Thus, the term "compatible ingredients" as used herein refers to the combination of particular culture media ingredients which, when mixed in solution either as concentrated or 1× formulations, are "stable" and "soluble."

The term "1× formulation" is meant to refer to any aqueous solution that contains some or all ingredients found in a cell culture medium at working concentrations. The "1× formulation" can refer to, for example, the cell culture medium or to any subgroup of ingredients for that medium. The concentration of an ingredient in a 1× solution is about the same as the concentration of that ingredient found in a cell culture formulation used for maintaining or cultivating cells in vitro. A cell culture medium used for the in vitro cultivation of cells is a 1× formulation by definition. When a number of ingredients are present, each ingredient in a 1× formulation has a concentration about equal to the concentration of each respective ingredient in a medium during cell culturing. For example, RPMI-1640 culture medium contains, among other ingredients, 0.2 g/L L-arginine, 0.05 g/L L-asparagine, and 0.02 g/L L-aspartic acid. A "1× formulation" of these amino acids contains about the same concentrations of these ingredients in solution. Thus, when referring to a "1× formulation," it is intended that each ingredient in solution has the same or about the same concentration as that found in the cell culture medium being described. The concentrations of ingredients in a 1× formulation of cell culture medium are well known to those of ordinary skill in the art. See, for example, *Methods For Preparation of Media, Supplements and Substrate For Serum-Free Animal Cell Culture* Allen R. Liss, N.Y. (1984), *Handbook of Microbiological Media*, Second Ed., Ronald M. Atlas, ed. Lawrence C. Parks (1997) CRC Press, Boca Raton, Fla. and *Plant Culture Media*, Vol. 1: Formulations and Uses E. F.

George, D. J. M. Puttock, and H. J. George (1987) Exegetics Ltd. Edington, Westbury, Wilts, BA13 4QG England each of which is incorporated by reference herein in its entirety. The osmolarity and/or pH, however, can differ in a 1× formulation compared to the culture medium, particularly when fewer ingredients are contained in the 1× formulation.

A "10× formulation" is meant to refer to a solution wherein the concentration of each ingredient in that solution is about 10 times more than the concentration of each respective ingredient in a medium during cell culturing. For example, a 10× formulation of RPMI-1640 culture medium can contain, among other ingredients, 2.0 g/L L-arginine, 0.5 g/L L-asparagine, and 0.2 g/L L-aspartic acid (compare 1× formulation, above). A "10× formulation" can contain a number of additional ingredients at a concentration about 10 times that found in the 1× culture formulation. As will be readily apparent, "25× formulation," "50× formulation," "100× formulation," "500× formulation," and "1000× formulation" designate solutions that contain ingredients at about 25-, 50-, 100-, 500-, or 1000-fold concentrations, respectively, as compared to a 1× cell culture formulation. Again, the osmolarity and pH of the medium formulation and concentrated solution can vary.

The term "trace element" or "trace element moiety" refers to a moiety which is present in a cell culture medium in only very low (i.e., "trace") amounts or concentrations, relative to the amounts or concentrations of other moieties or components present in the culture medium. In the present invention, these terms encompass $Ag^+$, $Al^{3+}$, $Ba^{2+}$, $Cd^{2+}$, $Co^{2+}$, $Cr^{3+}$, $Cu^{1+}$, $Cu^{2+}$, $Fe^{2+}$, $Fe^{3+}$, $Ge^{4+}$, $Se^{4+}$, $Br^-$, $I^-$, $Mn^{2+}$, $F^-$, $Si^{4+}$, $V^{5+}$, $Mo^{6+}$, $Ni^{2+}$, $Rb^+$, $Sn^{2+}$ and $Zr^{4+}$ and salts thereof. For example, the following salts can be used as trace elements in the culture media of the invention: $AgNO_3$, $AlCl_3 \cdot 6H_2O$, $Ba(C_2H_3O_2)_2$, $CdSO_4 \cdot 8H_2O$, $COCl_2 \cdot 6H_2O$, $Cr_2(SO_4)_3 \cdot 1H_2O$, $GeO_2$, $Na_2SeO_3$, $H_2SeO_3$, KBr, KI, $MnCl_2 \cdot 4H_2O$, NaF, $Na_2SiO_3 \cdot 9H_2O$, $NaVO_3$, $(NH_4)_6Mo_7O_{24} \cdot 4H_2O$, $NiSO_4 \cdot 6H_2O$, RbCl, $SnCl_2$, and $ZrOCl_2 \cdot 8H_2O$. Suitable concentrations of trace element moieties can be determined by one of ordinary skill in the art using only routine experimentation.

The term "amino acid" refers to amino acids or their derivatives (e.g., amino acid analogs), as well as their D- and L-forms. Examples of such amino acids include glycine, L-alanine, L-asparagine, L-cysteine, L-aspartic acid, L-glutamic acid, L-phenylalanine, L-histidine, L-isoleucine, L-lysine, L-leucine, L-glutamine, L-arginine, L-methionine, L-proline, L-hydroxyproline, L-serine, L-threonine, L-tryptophan, L-tyrosine, and L-valine, N-acetyl cysteine.

A "serum-free medium" is a medium that contains no serum (e.g., fetal bovine serum (FBS), calf serum, horse serum, goat serum, human serum, etc.) and is generally designated by the letters SFM.

The terms "serum-free culture conditions" and "serum-free conditions" refer to cell culture conditions that exclude serum of any type. These terms can be used interchangeably.

A "chemically defined" medium is one in which each chemical species and its respective quantity is known prior to its use in culturing cells. A chemically defined medium is made without lysates or hydrolysates whose chemical species are not known and/or quantified. A chemically defined medium is one preferred embodiment of the medium of the present invention.

The phrase "protein-free" culture media refers to culture media that contain no protein (e.g., no serum proteins such as serum albumin or attachment factors, nutritive proteins such as growth factors, or metal ion carrier proteins such as transferrin, ceruloplasmin, etc.). Preferably, if peptides are present, the peptides are smaller peptides, e.g., di- or tri-peptides. Preferably, peptides of deca-peptide length or greater are less than about 1%, more preferably less than about 0.1%, and even more preferably less than about 0.01% of the amino acids present in the protein free medium.

The phrase "low-protein" culture media as used herein refers to media that contain only low amounts of protein (typically less than about 10%, less than about 5%, less than about 1%, less than about 0.5%, or less than about 0.1%, of the amount or concentration of total protein found in culture media containing standard amounts of protein, such as standard basal medium supplemented with 5-10% serum).

The term "animal derived" material as used herein refers to material that is derived in whole or in part from an animal source, including recombinant animal DNA or recombinant animal protein DNA. Preferred media contain no animal desired material.

By "transition element" or "transition metal" (which can be used interchangeably) is meant an element in which an inner electron valence shell, rather than an outer shell, is only partially filled, such that the element acts as a transitional link between the most and least electropositive in a given series of elements. Transition elements are typically characterized by high melting points, high densities, high dipole or magnetic moments, multiple valencies, and the ability to form stable complex ions. Examples of such transition elements useful in the present invention include scandium (Sc), titanium (Ti), vanadium (V), chromium (Cr), manganese (Mn), iron (Fe), cobalt (Co), nickel (Ni), copper (Cu), zinc (Zn), yttrium (Y), zirconium (Zr), niobium (Nb), molybdenum (Mo), technetium (Tc), ruthenium (Ru), rhodium (Rh), palladium (Pd), silver (Ag), cadmium (Cd), lanthanum (La), hafnium (Hf), tantalum (Ta), tungsten (W), rhenium (Re), osmium (Os), iridium (Ir), platinum (Pt), gold (Au), mercury (Hg), and actinium (Ac). Of particular interest as a transition element for use in culture media compositions, including those of the present invention, are ions, chelates, salts, and complexes of iron ($Fe^{++}$ or $Fe^{+++}$).

A variety of techniques and reagents are available for the introduction of macromolecules into a target cell. Commonly used reagents include, for example, calcium phosphate, DEAE-dextran and lipids. For examples of detailed protocols for the use of reagents of these types, numerous references texts are available for example, Current Protocols in Molecular Biology, Chapter 9, Ausubel, et al. Eds., John Wiley and Sons, 1998.

Lipid aggregates such as liposomes have been found to be useful as agents for the delivery of macromolecules into cells. In particular, lipid aggregates comprising one or more cationic lipids have been demonstrated to be extremely efficient at the delivery of anionic macromolecules (for example, nucleic acids) into cells. One commonly used cationic lipid is N-[1-(2,3-dioleoyloxy)propyl]-N,N,N-trimethylammonium chloride (DOTMA). Liposomes comprising DOTMA alone or as a 1:1 mixture with dioleoylphosphatidylethanolamine (DOPE) have been used to introduce nucleic acids into cells. A 1:1 mixture of DOTMA:DOPE is commercially available from Invitrogen Corporation, Carlsbad, Calif. under the trade name of LIPOFECTIN®. Another cationic lipid that has been used to introduce nucleic acids into cells is 1,2-bis(oleoyl-oxy)-3-3-(trimethylammonia) propane (DOTAP). DOTAP differs from DOTMA in that the oleoyl moieties are linked to the propylamine backbone via ether bonds in DOTAP whereas they are linked via ester bonds in DOTMA. DOTAP is believed to be more readily degraded by the target cells. A structurally related group of compounds wherein one of the methyl groups of the trimethylammonium moiety is replaced with a hydroxyethyl group are similar in structure to the Rosenthal inhibitor (RI) of phospholipase A (see Rosenthal, et al., (1960) *J. Biol. Chem.* 233:2202-2206.). The RI has stearoyl esters linked to the propylamine core. The dioleoyl analogs of RI are commonly abbreviated DORI-ether and DORI-ester, depending upon the linkage of the lipid moiety to the propylamine core. The hydroxyl group of the hydroxyethyl moiety can be further derivatized, for example, by esterification to carboxyspermine.

Another class of compounds which has been used for the introduction of macromolecules into cells comprise a carboxyspermine moiety attached to a lipid (see, Behr, et al., (1989) *Proceedings of the National Academy of Sciences, USA* 86:6982-6986 and EPO 0 394 111). Examples of compounds of this type include dipalmitoylphosphatidylethanolamine 5-carboxyspermylamide (DPPES) and 5-carboxyspermylglycine dioctadecylamide (DOGS). DOGS is commercially available from Promega, Madison, Wis. under the trade name of TRANSFECTAM™.

A cationic derivative of cholesterol (3β-[N—(N',N'-dimethylaminoethane)-carbamoyl] cholesterol, DC-Chol) has been synthesized and formulated into liposomes with DOPE (see Gao, et al., (1991) BBRC 179(1):280-285.) and used to introduce DNA into cells. The liposomes thus formulated were reported to efficiently introduce DNA into the cells with a low level of cellular toxicity. Lipopolylysine, formed by conjugating polylysine to DOPE (see Zhou, et al., (1991) BBA 1065:8-14), has been reported to be effective at introducing nucleic acids into cells in the presence of serum.

Other types of cationic lipids that have been used to introduce nucleic acids into cells include highly packed polycationic ammonium, sulfonium and phosphonium lipids such as those described in U.S. Pat. Nos. 5,674,908 and 5,834,439, and international application no. PCT/US99/26825, published as WO 00/27795. One preferred agent for delivery of macromolecules is LIPOFECTAMINE 2000™ which is available from Invitrogen. See U.S. international application no. PCT/US99/26825, published as WO 00/27795.

A "reagent for the introduction of macromolecules" into cells is any material known to those of skill in the art which facilitates the entry of a macromolecule into a cell. For example, see U.S. Pat. No. 5,279,833. In some embodiments, the reagent can be a "transfection reagent" and can be any compound and/or composition that increases the uptake of one or more nucleic acids into one or more target cells. A variety of transfection reagents are known to those skilled in the art. Suitable transfection reagents can include, but are not limited to, one or more compounds and/or compositions comprising cationic polymers such as polyethyleneimine (PEI), polymers of positively charged amino acids such as polylysine and polyarginine, positively charged dendrimers and fractured dendrimers, cationic β-cyclodextrin containing polymers (CD-polymers), DEAE-dextran and the like. In some embodiments, a reagent for the introduction of macromolecules into cells can comprise one or more lipids which can be cationic lipids and/or neutral lipids. Preferred lipids include, but are not limited to, N-[1-(2,3-dioleyloxy)propyl]-N,N,N-trimethylamonium chloride (DOTMA), dioleoylphosphatidylcholine (DOPE), 1,2-Bis(oleoyloxy)-3-(4'-trimethylammonio) propane (DOTAP), 1,2-dioleoyl-3-(4'-trimethylammonio) butanoyl-sn-glycerol (DOTB), 1,2-dioleoyl-3-succinyl-sn-glycerol choline ester (DOSC), cholesteryl (4'-trimethylammonio)butanoate (ChoTB), cetyltrimethyl ammonium bromide (CTAB), 1,2-dioleoyl-3-dimethyl-hydroxyethyl ammonium bromide (DORI), 1,2-dioleyloxypropyl-3-dimethyl-hydroxyethyl ammonium bromide (DORIE), 1,2-dimyristyloxypropyl-3-dimethyl-hydroxyethyl ammonium bromide (DMRIE), O,O'-didodecyl-N-[p(2-trimethylammonioethyloxy)benzoyl]-N,N,N-trimethylammonium chloride, spermine conjugated to one or more lipids (for example, 5-carboxyspermylglycine dioctadecylamide (DOGS), N,N$^I$,N$^{II}$,N$^{III}$-tetramethyl-N,N$^I$,N$^{II}$,N$^{III}$-tetrapalmitylspermine (TM-TPS) and dipalmitoyl-phosphatidylethanolamine 5-carboxyspermylaminde (DPPES)), lipopolylysine (polylysine conjugated to DOPE), TRIS (Tris(hydroxymethyl)aminomethane, tromethamine) conjugated fatty acids (TFAs) and/or peptides such as trilysyl-alanyl-TRIS mono-, di-, and tri-palmitate, (3β-[N—(N', N'-dimethylaminoethane)-carbamoyl] cholesterol (DC-Chol), N-(α-trimethylammonioacetyl)-didodecyl-D-glutamate chloride (TMAG), dimethyl dioctadecylammonium bromide (DDAB), 2,3-dioleyloxy-N-[2(spermine-carboxamido)ethyl]-N,N-dimethyl-1-propanamininiumtrifluoroacetate (DOSPA) and combinations thereof.

Those skilled in the art will appreciate that certain combinations of the above mentioned lipids have been shown to be particularly suited for the introduction of nucleic acids into cells for example a 3:1 (w/w) combination of DOSPA and DOPE is available from Invitrogen Corporation, Carlsbad, Calif. under the trade name LIPOFECTAMINE™, a 1:1 (w/w) combination of DOTMA and DOPE is available from Invitrogen Corporation, Carlsbad, Calif. under the trade name LIPOFECTIN®, a 1:1 (M/M) combination of DMRIE and cholesterol is available from Invitrogen Corporation, Carlsbad, Calif. under the trade name DMRIE-C reagent, a 1:1.5 (M/M) combination of TM-TPS and DOPE is available from Invitrogen Corporation, Carlsbad, Calif. under the trade name CellFECTIN® and a 1:2.5 (w/w) combination of DDAB and DOPE is available from Invitrogen Corporation, Carlsbad, Calif. under the trade name LipfectACE®. In addition to the above-mentioned lipid combinations, other formulations comprising lipids in admixture with other compounds, in particular, in admixture with peptides and proteins comprising nuclear localization sequences, are known to those skilled in the art. For example, see international application no. PCT/US99/26825, published as WO 00/27795.

The present invention is directed to a culture medium that supports (a) the introduction of at least one macromolecule into eukaryotic cells in culture, (b) the cultivation of cells into which at least one macromolecule is introduced, and optionally (c) the production of protein product or expression of the nucleic acid in cells into which at least one macromolecule is introduced, wherein medium containing the macromolecule does not need to be removed from the culture and replaced with fresh medium after introduction of at least one macromolecule into cells and prior to cultivation and production of protein product or expression of nucleic acid. Using the medium of the present invention, it is not necessary to replenish, replace or supplement the medium after one has introduced at least on emacromolecule into at least one cell, and before cells into which at least one macromolecule has been introduced are further cultured to produces protein product or express a nucleic acid. In the medium, methods, kit and composition of the present invention, the medium is a serum-free medium and/or a chemically defined medium and/or protein free or low protein medium and/or a medium that does not contain animal derived components, or a medium having combinations of these features.

CD CHO medium (Invitrogen Corporation, Carlsbad, Calif.) can be used to transfect CHO cells in suspension culture. However, transfection of CHO cells in CD CHO medium works only if the cells are transfected with nucleic acid in a relatively much smaller volume of CD CHO medium than the transfected cells are to be cultured in after transfection. Thus, for cells to be cultured in CD CHO medium after they are transfected with nucleic acid, it is necessary to transfect cells in a relatively small volume, and then dilute the transfected cells in a relatively much larger volume of CD CHO medium for subsequent culturing.

In a preferred embodiment, with respect to the introduction of compounds or macromolecules (e.g., nucleic acid) into cells in culture, the culture medium of the present invention facilitates higher cell transformation efficiency than does CD CHO medium, and/or does not require transfecting in a smaller volume than cells are to be cultured in after transfection, and/or facilitates higher cell viability than does CD CHO medium, and/or facilitates higher cell density (i.e., cells/ml of culture medium) than does CD CHO medium, and/or facilitates a higher level of recombinant protein expression in cells in culture than does CD CHO medium. Preferably, the same volume of medium is used for introduction of at least one macromolecule or transfection and subsequent cultivation. Alternatively, the cells are divided or medium volume is increased less from about 2, about 5, about 8 or about 10 times. In preferred embodiments, the culture medium of the present invention is not CD CHO medium.

The medium, methods, kit and composition of the present invention are intended to be used to introduce at least one macromolecule or to transfect and culture cells in any volume of culture medium. Such introduction is preferably accomplished in 0.1 to 10 times the amount of medium used to culture cells to be transfected. Preferably, the cell culture volume is greater than about one milliliter. More preferably, the cell culture volume is from about one milliliter to 250 liters. More preferably, the cell culture volume is from about 30 ml to about 50 liters. More preferably, the cell culture volume is from about 100 ml to about 50 liters. More preferably, the cell culture volume is from about 500 ml to about 50 liters. More preferably, the cell culture volume is from about 500 ml to about 25 liters. More preferably, the cell culture volume is from about 500 ml to about 10 liters. More preferably, the cell culture volume is from about 500 ml to about 5 liters. More preferably, the cell culture volume is from about 500 ml to about 1 liter.

In the medium, methods, kit and composition of the present invention, the medium preferably does not contain compounds that can interfere with introduction of macromolecules or transfection, e.g., polyanionic compounds such as polysulfonated and/or polysulfated compounds. Preferably, the medium does not contain dextran sulfate.

The medium, methods, kit and composition of the present invention permit the introduction of compounds or macromolecules (particularly macromolecules, for example nucleic acids, proteins and peptides) into the cultured cells (for example by transfection) without the need to change the medium. In one preferred embodiment, the present invention provides a medium for the cultivation and transfection of eukaryotic cells.

Using the medium, methods, kit and composition of the present invention, those of ordinary skill in the art can introduce macromolecules or compounds (e.g., nucleic acid) into cells in culture. Preferably, the macromolecule or compound (e.g., nucleic acid) is introduced into at least about 20 percent of the cells. More preferably, the macromolecule or compound (e.g., nucleic acid) is introduced into about 20 to about 100 percent of the cells. More preferably, the macromolecule or compound (e.g., nucleic acid) is introduced into about 30 to about 100 percent of the cells. More preferably, the macromolecule or compound (e.g., nucleic acid) is introduced into about 50 to about 100 percent of the cells. Practically, the macromolecule or compound might be introduced into about 20% to about 90% of the cells, about 20% to about 80% of the cells, about 30% to about 60, 70, 80 or 90% of the cells, about 20, 30, 40 or 50% to about 70, 75, 80, 85, 90, 95 or 98% of the cells, etc. Even about 60, 70, 75 or 80 to about 90% or close to 100% of the cells may contain the introduced molecule or compound.

In preferred embodiments of the medium, methods, kit and composition of the present invention, one or more undesirable components (i.e., one or more serum components, one or more undefined components, one or more protein components and/or one or more animal derived components) have been substituted or replaced in one or more functions by one or more replacement compounds. Replacement compounds of the invention can be metal binding compounds and/or one or more transition element complexes, said complexes comprising one or more transition elements or a salts or ions thereof, in a complex with one or more metal-binding compounds. Preferably, the medium is capable of supporting the cultivation of a cell in vitro in the absence of one or more naturally derived metal carriers, such as transferrin, or other animal derived proteins or extracts. The metal binding compound can be in a complex with a transition metal prior to addition of the metal binding compound to the medium. In other embodiments, the metal binding compound is not in a complex with a transition metal prior to addition of the metal binding compound to the media. Preferably, the medium of the present invention does not contain transferrin and/or does not contain insulin.

The present invention also relates to a cell culture medium obtained by combining a medium with one or more replacement compounds. Preferably, the medium can be a serum-free medium and/or a chemically defined medium and/or a protein-free or low protein medium and/or can be a medium lacking animal derived components. The medium preferably does not contain transferrin and/or does not contain insulin. In some preferred embodiments, the medium can be capable of supporting the cultivation of a cell in vitro and/or can permit the introduction of macromolecules into the cell. In some embodiments, one or more of the replacement compounds can be a metal binding compound and/or can be a transition element complex, said complex comprising at least one transition element or a salt or ion thereof complexed to at least one metal-binding compound. Preferred transition elements, metal-binding compounds, and transition element complexes for use in this aspect of the invention include those described in detail herein.

Replacement compounds of the present invention can facilitate the delivery of transition metals to cells cultured in vitro. In preferred embodiments, the replacement compounds can deliver iron and replace transferrin. A preferred replacement compound is a hydroxypyridine derivative. Preferably, the hydroxypyridine derivative is selected from the group consisting of 2-hydroxypyridine-N-oxide, 3-hydroxy-4-pyrone, 3-hydroxypypyrid-2-one, 3-hydroxypyrid-2-one, 3-hydroxypyrid-4-one, 1-hydroxypyrid-2-one, 1,2-dimethyl-3-hydroxypyrid-4-one, 1-methyl-3-hydroxypyrid-2-one, 3-hydroxy-2(1H)-pyridinone, and pyridoxal isonicotinyl hydrazone, nicotinic acid-N-oxide, 2-hydroxynicotinic acid. Most preferably, the hydroxypyridine derivative is 2-hydroxypyridine-N-oxide.

The replacement compounds of the present invention can be used with any media, including media for cultivating or growing eukaryotic and/or prokaryotic cells, tissues, organs, etc. Such media include, but are not limited to, Dulbecco's Modified Eagle's Medium (DMEM), Minimal Essential Medium (MEM), Basal Medium Eagle (BME), RPMI-1640, Ham's F-10, Ham's F-12, αMinimal Essential Medium (αMEM), Glasgow's Minimal Essential Medium (G-MEM), and Iscove's Modified Dulbecco's Medium (IMDM). Other media that are commercially available (e.g., from Invitrogen Corporation, Carlsbad, Calif.) or that are otherwise known in the art can be equivalently used in accordance with the present invention including, but not limited to, 293 SFM, CD-CHO medium, VP SFM, BGJb medium, Brinster's BMOC-3 medium, cell culture freezing medium, CMRL media, EHAA medium, eRDF medium, Fischer's medium, Gamborg's B-5 medium, GLUTAMAX™ supplemented media, Grace's insect cell media, HEPES buffered media, Richter's modified MEM, IPL-41 insect cell medium, Leibovitz's L-15 media, McCoy's 5A media, MCDB 131 medium, Media 199, Modified Eagle's Medium (MEM), Medium NCTC-109, Schneider's Drosophila medium, TC-100 insect medium, Waymouth's MB 752/1 media, William's Media E, protein free hybridoma medium II (PFHM II), AIM V media, Keratinocyte SFM, defined Keratinocyte SFM, STEMPRO® SFM, STEMPRO® complete methylcellulose medium, HepatoZYME-SFM, Neurobasal™ medium, Neurobasal-A medium, Hibernate™ A medium, Hibernate E medium, Endothelial SFM, Human Endothelial SFM, Hybridoma SFM, PFHM II, Sf 900 medium, Sf 900 II SFM, EXPRESS FIVE® medium, CHO-S-SFM, AMINOMAX-II complete medium, AMINOMAX-C100 complete medium, AMINOMAX-C100 basal medium, PB-MAX™ karyotyping medium, KARYOMAX bone marrow karyotyping medium, KNOCKOUT D-MEM and $CO_2$ independent medium. The above media are obtained from manufacturers known to those of ordinary skill in the art, such as JRH, Sigma, HyClone, and BioWhittaker. Additional examples of media suitable for use in the practice of the present invention can be found in U.S. Pat. Nos. 5,135,866 and 5,232,848 as well as in international publications nos. WO 88/02774, WO 98/15614, WO 98/08934 and European patent no. 0 282 942, the entireties of which are specifically incorporated herein by reference.

The present invention also provides a method for introducing macromolecules into cells, comprising culturing cells in a medium of the invention and contacting the cells in the medium with one or more macromolecules under conditions causing the macromolecules to be taken up by one or more of the cells. Preferably, the medium is a serum-free medium and/or a chemically defined medium and/or a protein-free or low protein medium and/or can be a medium lacking animal derived components. Preferred cells include eukaryotic cells. More preferably, the cells are mammalian cells. The medium can comprise one or more replacement compounds and preferably does not contain transferrin and/or does not contain insulin. In some preferred embodiments, the medium permits the growth and transfection of the cell in the same medium. In some embodiments, the macromolecules can comprise one or more nucleic acids and conditions causing the nucleic acid molecules to be taken up by the cells include contacting the nucleic acid with a reagent which causes the nucleic acid to be introduced into one or more cells.

The present invention also provides a composition comprising a medium of the invention and a cell. Preferably, the medium is a serum-free medium and/or a chemically defined medium and/or a protein-free or low protein medium and/or a medium lacking animal derived components. Preferred cells include eukaryotic cells. More preferably, the cells are mammalian cells. The medium can comprise one or more replacement compounds and preferably does not contain transferrin and/or does not contain insulin. Preferably, the medium supports the growth and transfection of the cell in the same medium.

The present invention also provides compositions comprising a medium of the present invention and one or more reagents for the introduction of macromolecules into one or more cells. Preferably, the medium is a serum-free medium and/or a chemically defined medium and/or a protein-free or low protein medium and/or a medium lacking animal derived components. The medium can comprise one or more replacement compounds and preferably does not contain transferrin and/or does not contain insulin. Preferably, the medium contains a transfection reagent and the macromolecules are nucleic acids. The macromolecules might also be proteins and/or peptides. In some embodiments, the reagent comprises one or more lipids of which one or more can be cationic lipids. More preferably, the reagent comprises a mixture of neutral and cationic lipids. In some embodiments, the reagent comprises one or more peptides and/or proteins which can be provided alone or in admixture with one or more lipids.

The present invention also provides compositions comprising a medium of the invention and one or more macromolecules to be introduced into a cell. Preferably, the medium is a serum-free medium and/or a chemically defined medium and/or a protein-free or low protein medium and/or a medium lacking animal derived components. The medium can comprise one or more replacement compounds and preferably does not contain transferrin and/or does not contain insulin. The macromolecules can be, for example, nucleic acids and/or proteins and/or peptides and can be uncomplexed or can be in the form of a complex with one or more reagents for the introduction of macromolecules into cells. Preferably, the macromolecules are nucleic acids and can be in the form of a complex with one or more transfection reagents.

The present invention also provides a composition comprising at least one component (or combination thereof) selected from the group consisting of a medium of the present invention, at least one cell, at least one macromolecule, at least one reagene for introducing at least one macromolecule into at least one cell. Preferably, the cells are eukaryotic cells. More preferably, the cells are mammalian cells. Preferably, the medium is a serum-free medium and/or a chemically defined medium and/or a protein-free or low protein medium and/or a medium lacking animal derived components. The medium can comprise one or more replacement compounds and preferably does not contain transferrin and/or does not contain insulin. In some preferred embodiments, the reagent is a transfection reagent and the macromolecules are nucleic acids, for example RNA and/or DNA. Alternatively, the macromolecules are proteins and/or peptides.

In some embodiments, the reagent comprises one or more lipids of which one or more can be cationic lipids. More preferably, the reagent comprises a mixture of neutral and cationic lipids. In some embodiments, the reagent comprises one or more peptides and/or proteins which can be provided alone or in admixture with one or more lipids. In preferred embodiments, the reagent complexes with the macromolecule to introduce the macromolecule into the cell.

The present invention also provides kits for the culture and transfection of cells comprising at least one container comprising a medium for the culture and transfection of cells. Such kits may also comprise at least one component (or a combination thereof) selected from the group consisting of a medium of the present invention, at least one cell, at least one macromolecule, at least one reagent for introducing at least one macromolecule into at least one cell, at least one buffer or buffering salt, and instructions for using the kit to introduce at least one macromolecule into at least one cell. Preferably, the medium is a serum-free medium and/or a chemically defined medium and/or a protein-free or low protein medium and/or a medium lacking animal derived components. The medium can comprise one or more replacement compounds and preferably does not contain transferrin and/or does not contain insulin and/or does not contain an animal growth factor. The medium can comprise one or more replacement compounds which can be metal binding compounds and/or can comprise one or more complexes comprising one or more replacement compounds. In some embodiments, the medium can comprise one or more complexes, said complex comprising one or more transition elements or salts or ions thereof complexed one or more replacement compounds which can be metal-binding compounds. In some embodiments, said medium is capable of supporting the cultivation of a cell in vitro and permits transfection of cells cultured therein. In some embodiments, kits of the invention can further comprise at least one container comprising a lipid for transfecting cells. In some embodiments, the kits of the invention can comprise at least one container comprising a nucleic acid.

According to one aspect of the invention, a transition element is preferably selected from the group consisting of scandium, titanium, vanadium, chromium, manganese, iron, cobalt, nickel, copper, zinc, yttrium, zirconium, niobium, molybdenum, technetium, rubidium, rhodium, palladium, silver, cadmium, lanthanum, hafnium, tantalum, tungsten, rhenium, osmium, iridium, platinum, gold, mercury, and actinium, or salts or ions thereof, and is preferably an iron salt. Suitable iron salts include, but are not limited to, $FeCl_3$, $Fe(NO_3)_3$ or $FeSO_4$ or other compounds that contain $Fe^{+++}$ or $Fe^{++}$ ions.

Preferred replacement compounds include, but are not limited to, metal-binding compounds. See, for example, international patent application no. PCT/US00/23580, publication no. WO 01/16294.

Metal binding compounds of the present invention include any macromolecules which can interact with or bind with transition elements and facilitate their uptake by cells. Such interaction/binding can be covalent or non-covalent in nature. The metal-binding compound used in this aspect of the invention is preferably selected from the group consisting of a polyol, a hydroxypyridine derivative, 1,3,5-N,N', N''-tris(2,3-dihydroxybenzoyl)amino-methylbenzene, ethylenediamine-N,N'-tetramethylenephosphonic acid, trisuccin, an acidic saccharide (e.g., ferrous gluconate), a glycosaminoglycan, diethylenetriaminepentaacetic acid, nicotinic acid-N-oxide, 2-hydroxy-nicotinic acid, mono-, bis-, or tris-substituted 2,2'-bipyridine, a hydroxamate derivative (e.g. acetohydroxamic acid), an amino acid derivative, deferoxamine, ferrioxamine, iron basic porphine and derivatives thereof, DOTA-lysine, a texaphyrin, a sapphyrin, a polyaminocarboxylic acid, an α-hydroxycarboxylic acid, a polyethylenecarbamate, ethyl maltol, 3-hydroxy-2-pyridine, and IRC011. In one preferred embodiment, the metal-binding compound is a polyol such as sorbitol or dextran, and particularly sorbitol. In a related embodiment, the metal-binding compound is a hydroxypyridine derivative, such as 2-hydroxypyridine-N-oxide, 3-hydroxy-4-pyrone, 3-hydroxypypyrid-2-one, 3-hydroxypyrid-2-one, 3-hydroxypyrid-4-one, 1-hydroxypyrid-2-one, 1,2-dimethyl-3-hydroxypyrid-4-one, 1-methyl-3-hydroxypyrid-2-one, 3-hydroxy-2(1H)-pyridinone, ethyl maltol or pyridoxal isonicotinyl hydrazone, and is preferably 2-hydroxypyridine-N-oxide. In particularly preferred embodiments according to this aspect of the invention, the transition metal complex can be a sorbitol-iron complex or 2-hydroxypyridine-N-oxide-iron complex. The metal binding compounds of the present invention can also bind divalent cations such as $Ca^{++}$ and $Mg^{++}$.

The invention relates to cell culture media comprising one or more replacement compounds which can be metal-binding compounds and further comprising one or more ingredients selected from the group of ingredients consisting of at least one amino acid (such as L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine or L-valine, N-acetyl-cysteine), at least one vitamin (such as biotin, choline chloride, D-Ca⁺⁺-pantothenate, folic acid, i-inositol, niacinamide, pyridoxine, riboflavin, thiamine or vitamin $B_{12}$), at least one inorganic salt (such as a calcium salt, $CuSO_4$, $FeSO_4$, $Fe(NO_3)_3$, $FeCl_3$, KCl, a magnesium salt, a manganese salt, sodium acetate, NaCl, $NaHCO_3$, $Na_2HPO_4$, $Na_2SO_4$, a selenium salt, a silicon salt, a molybdenum salt, a vanadium salt, a nickel salt, a tin salt, $ZnCl_2$, $ZnSO_4$ or other zinc salts), adenine, ethanolamine, D-glucose, one or more cytokines, heparin, hydrocortisone, lipoic acid, phenol red, phosphoethanolamine, putrescine, sodium pyruvate, triiodothyronine, PLURONIC F68, and thymidine.

The culture media of the present invention can optionally include one or more buffering agents. Suitable buffering agents include, but are not limited to, N-[2-hydroxyethyl]-piperazine-N'-[2-ethanesulfonic acid] (HEPES), MOPS, MES, phosphate, bicarbonate and other buffering agents suitable for use in cell culture applications. A suitable buffering agent is one that provides buffering capacity without substantial cytotoxicity to the cells cultured. The selection of suitable buffering agents is within the ambit of ordinary skill in the art of cell culture.

According to the invention, a medium suitable for use in forming the cell culture media of the invention can comprise one or more ingredients, and can be obtained, for example, by combining one or more ingredients selected from the group consisting of adenine, ethanolamine, D-glucose, heparin, a buffering agent, hydrocortisone, lipoic acid, phenol red, phosphoethanolamine, putrescine, sodium pyruvate, triiodothyronine, thymidine, L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-valine, N-acetyl-cysteine, biotin, choline chloride, D-Ca⁺⁺-pantothenate, folic acid, i-inositol, niacinamide, pyridoxine, riboflavin, thiamine, vitamin $B_{12}$, Pluronic F68, recombinant insulin, a calcium salt, $CuSO_4$, $FeSO_4$, $FeCl_3$, $Fe(NO_3)_3$, KCl, a magnesium salt, a manganese salt, sodium acetate, NaCl, $NaHCO_3$, $Na_2HPO_4$, $Na_2SO_4$, a selenium salt, a silicon salt, a molybdenum salt, a vanadium salt, a nickel salt, a tin salt, ZnCl$_2$, ZnSO$_4$ or other zinc salts, wherein each ingredient is added in an amount which supports the cultivation of a cell in vitro.

The invention is also directed to a cell culture medium comprising ingredients selected from ethanolamine, D-glucose, HEPES, insulin, linoleic acid, lipoic acid, phenol red, PLURONIC F68, putrescine, sodium pyruvate, transferrin, L-alanine, L-arginine, L-asparagine, L-aspartic acid, L-cysteine, L-glutamic acid, L-glutamine, glycine, L-histidine, L-isoleucine, L-leucine, L-lysine, L-methionine, L-phenylalanine, L-proline, L-serine, L-threonine, L-tryptophan, L-tyrosine, L-valine, biotin, choline chloride, D-Ca$^{++}$-pantothenate, folic acid, i-inositol, niacinamide, pyridoxine, riboflavin, thiamine, vitamin B$_{12}$, one or more calcium salts, Fe(NO$_3$)$_3$, KCl, one or more magnesium salts, one or more manganese salts, NaCl, NaHCO$_3$, Na$_2$HPO$_4$, one or more selenium salts, one or more vanadium salts and one or more zinc salts, wherein each ingredient is present in an amount which supports the suspension cultivation of a mammalian epithelial cell in vitro. The invention is also directed to such media which can optionally further comprise one or more supplements selected from the group consisting of one or more cytokines, heparin, one or more animal peptides, one or more yeast peptides and one or more plant peptides (most preferably one or more of rice, aloevera, soy, maize, wheat, pea, squash, spinach, carrot, potato, sweet potato, tapioca, avocado, barley, coconut and/or green bean, and/or one or more other plants), e.g., see international application no. PCT/US97/18255, published as WO 98/15614.

The above ingredients listed in the following Tables 1-3, when admixed together in solution, form a complete culture medium of the present invention. These complete media are suitable for use in the culture of a variety of mammalian cells, as described in more detail herein. Based on the information obtained in Tables 1-3, and knowledge possessed by those of ordinary skill in the art, one of ordinary skill in the art can obtain operative media formulations without undue experimentation.

TABLE 1

Preferred Ranges of Ingredients

| Component | Gram(s)/L (unless noted) about: |
|---|---|
| L-Arginine HCl | 0.05-2.50 |
| L-Asparagine | 0.005-0.05 |
| L-Aspartic Acid | 0.03-0.8 |
| L-Cysteine HCl H$_2$O | 0.03-0.8 |
| L-Glutamic Acid | 0.002-0.05 |
| L-Histidine HCl H$_2$O | 0.01-0.3 |
| L-Isoleucine | 0.04-1 |
| L-Leucine | 0.06-1.5 |
| L-Lysine HCl | 0.05-1.25 |
| L-Methionine | 0.02-0.6 |
| L-Phenylalanine | 0.02-0.5 |
| L-Serine | 0.07-2 |
| L-Threonine | 0.02-0.6 |
| L-Tryptophan | 0.008-0.2 |
| L-Valine | .03-1 |
| L-Tyrosine 2Na 2 H$_2$O | 0.02-0.5 |
| L-Glutamine (recommended addition, formulation does not contain) | 0.1-3 |
| D-Glucose (Dextrose) | 1-25 |
| Lipoic Acid | 0.0004-0.01 |
| Linoleic Acid | 0.00001-0.0003 |
| Folic Acid | 0.0001-003 |
| HEPES | 0.5-15 |

TABLE 1-continued

Preferred Ranges of Ingredients

| Component | Gram(s)/L (unless noted) about: |
|---|---|
| 2-Hydroxypyridine-n-oxide | 0.0006-0.02 |
| Pluronic F-68* | 0.06-2 |
| Sodium Phosphate Monobasic H$_2$O | 0.03-0.6 |
| Ammonium Meta Vanadate | 0.0000001-0.000003 |
| Manganous Chloride 4H$_2$O | 0.00000001-0.0000005 |
| Pyridoxine HCl | 0.0002-0.005 |
| Thiamine HCl | 0.0002-0.006 |
| Ferric Nitrate 9H$_2$O | 0.0002-0.004 |
| Magnesium Sulfate | 0.005-0.1 |
| Zinc Sulfate | 0.00008-0.002 |
| Zinc Chloride | 0.00005-0.001 |
| Ascorbic Acid | 0.00000005-0.0000003 |
| D-Calcium Pantothenate | 0.0002-0.006 |
| Calcium Chloride | 0.002-0.06 |
| Magnesium Chloride | 0.02-0.4 |
| Potassium Chloride | 0.06-1.2 |
| Sodium Selenite | 0.0000000001-0.00000003 |
| Vitamin B$_{12}$ | 0.00002-0.005 |
| Choline Chloride | 0.003-0.07 |
| i-Inositol | 0.004-0.09 |
| Niacinamide | 0.0002-0.006 |
| Ethanolamine HCl | 0.001-0.3 |
| Putrescine 2HCl | 0.00003-0.008 |
| Sodium Pyruvate | 0.02-0.6 |
| Riboflavin | 0.00004-0.001 |
| Biotin | 0.00002-0.0005 |
| Sodium Bicarbonate | 0.5 2 |
| Sodium Chloride *** | 0.6-16 *** |

*** Added to adjust osmolarity. Quantity will vary somewhat between formulations. NaCL is added to adjust osmo from ~160 to a value within 275 +/− 5 mOsmo

TABLE 2

Exemplary Medium

| Component | Gram(s)/L (unless noted) about: |
|---|---|
| L-Arginine HCl | 0.4 |
| L-Asparagine | 0.03 |
| L-Aspartic Acid | 0.2 |
| L-Cysteine HCl H$_2$O | 0.2 |
| L-Glutamic Acid | 0.01 |
| L-Histidine HCl H$_2$O | 0.06 |
| L-Isoleucine | 0.2 |
| L-Leucine | 0.3 |
| L-Lysine HCl | 0.2 |
| L-Methionine | 0.1 |
| L-Phenylalanine | 0.1 |
| L-Serine | 0.4 |
| L-Threonine | 0.1 |
| L-Tryptophan | 0.04 |
| L-Valine | 0.2 |
| L-Tyrosine 2Na 2 H$_2$O | 0.1 |
| L-Glutamine (recommended addition, formulation does not contain) | 0.6 |
| D-Glucose (Dextrose) | 5 |
| Lipoic Acid | 0.002 |
| Linoleic Acid | 0.00006 |
| Folic Acid | 0.0005 |
| HEPES | 3.0 |
| 2-Hydroxypyridine-n-oxide | 0.003 |
| Pluronic F-68* | 0.3 |
| Sodium Phosphate Monobasic H$_2$O | 0.1 |
| Ammonium Meta Vanadate | 0.0000006 |

TABLE 2-continued

Exemplary Medium

| Component | Gram(s)/L (unless noted) about: |
|---|---|
| Manganous Chloride 4H$_2$O | 0.0000001 |
| Pyridoxine HCl | 0.001 |
| Thiamine HCl | 0.001 |
| Ferric Nitrate 9H$_2$O | 0.0008 |
| Magnesium Sulfate | 0.02 |
| Zinc Sulfate | 0.0004 |
| Zinc Chloride | 0.0003 |
| Ascorbic Acid | 0.0000003 |
| D-Calcium Pantothenate | 0.001 |
| Calcium Chloride | 0.01 |
| Magnesium Chloride | 0.08 |
| Potassium Chloride | 0.3 |
| Sodium Selenite | 0.000000007 |
| Vitamin B$_{12}$ | 0.001 |
| Choline Chloride | 0.01 |
| i-Inositol | 0.02 |
| Niacinamide | 0.001 |
| Ethanolamine HCl | 0.005 |
| Putrescine 2HCl | 0.0002 |
| Sodium Pyruvate | 0.1 |
| Riboflavin | 0.0002 |
| Biotin | 0.0001 |
| Sodium Bicarbonate | 2.0 |
| Sodium Chloride *** | 3.0 *** |

*** Added to adjust osmolarity. Quantity will vary somewhat between formulations. NaCL is added to adjust osmo from ~160 to a value within 275 +/− 5 mOsmo

TABLE 3

Well Defined Medium

| Component | Gram(s)/L (unless noted) about: | Component | Gram(s)/L (unless noted) about: |
|---|---|---|---|
| L-Arginine HCl | 0.43 | Ammonium Meta Vanadate | 0.0000006 |
| L-Asparagine | 0.0264 | Manganous Chloride 4H$_2$O | 0.0000001 |
| L-Aspartic Acid | 0.15 | Pyridoxine HCl | 0.00103 |
| L-Cysteine HCl H$_2$O | 0.15 | Thiamine HCl | 0.00112 |
| L-Glutamic Acid | 0.01 | Ferric Nitrate 9H$_2$O | 0.00081 |
| L-Histidine HCl H$_2$O | 0.06 | Magnesium Sulfate | 0.0241 |
| L-Isoleucine | 0.2 | Zinc Sulfate | 0.000375 |
| L-Leucine | 0.3 | Zinc Chloride | 0.00025 |
| L-Lysine HCl | 0.25 | Ascorbic Acid | 0.00000025 |
| L-Methionine | 0.115 | D-Calcium Pantothenate | 0.00119 |
| L-Phenylalanine | 0.1 | Calcium Chloride | 0.0111 |
| L-Serine | 0.388 | Magnesium Chloride | 0.0762 |
| L-Threonine | 0.12 | Potassium Chloride | 0.2763 |
| L-Tryptophan | 0.04 | Sodium Selenite | 0.0000000067 |
| L-Valine | 0.19 | Vitamin B$_{12}$ | 0.00103 |
| L-Tyrosine 2Na 2 H$_2$O | 0.1 | Choline Chloride | 0.014 |
| L-Glutamine (recommended addition, formulation does not contain) | 0.584 | i-Inositol | 0.018 |
| D-Glucose (Dextrose) | 5 | Niacinamide | 0.00122 |
| Lipoic Acid | 0.002 | Ethanolamine HCl | 0.005 |
| Linoleic Acid | 0.00006 | Putrescine 2HCl | 0.00016 |
| Folic Acid | 0.0005 | Sodium Pyruvate | 0.11 |
| HEPES | 2.98 | Riboflavin | 0.00022 |
| 2-Hydroxypyridine-n-oxide | 0.003 | Biotin | 0.000097 |
| Pluronic F-68* | 0.3 | Sodium Bicarbonate | 2.4 |
| Sodium Phosphate Monobasic H$_2$O | 0.125 | Sodium Chloride *** | 3.126 *** |

*** Added to adjust osmolarity. Quantity will vary somewhat between formulations. NaCL is added to adjust osmo from ~160 to a value within 275 +/− 5 mOsmo The media provided by the present invention can be protein-free, and can be a 1× formulation or concentrated as, for example, a 10×, 20×, 25×, 50×, 100×, 500×, or 1000× medium formulation.

The media of the invention can also be prepared in different forms, such as dry powder media ("DPM"), a granulated preparation (which requires addition of water, but not other processing, such as pHing), liquid media or as media concentrates.

The basal medium that is a medium useful only for maintenance, but not for growth or production of product, can comprise a number of ingredients, including amino acids, vitamins, organic and inorganic salts, sugars and other components, each ingredient being present in an amount which supports the cultivation of a mammalian epithelial cell in vitro.

In the medium, methods, kit and composition of the present invention, the medium can be used to culture a variety of cells. Preferably, the medium is used to culture eukaryotic cells. More preferably, the medium is used to culture plant and/or animal cells. More preferably, the medium is used to culture mammalian cells, fish cells, insect cells, amphibian cells or avian cells. More preferably, the medium is used to culture mammalian cells. More preferably, the medium is used to culture mammalian cells, including primary epithelial cells (e.g., keratinocytes, cervical epithelial cells, bronchial epithelial cells, tracheal epithelial cells, kidney epithelial cells and retinal epithelial cells) and established cell lines and their strains (e.g., 293 embryonic kidney cells, BHK cells, HeLa cervical epithelial cells and PER-C6 retinal cells, MDBK (NBL-1) cells, 911 cells, CRFK cells, MDCK cells, CHO cells, BeWo cells, Chang cells, Detroit 562 cells, HeLa 229 cells, HeLa S3 cells, Hep-2 cells, KB cells, LS 180 cells, LS 174T cells, NCI-H-548 cells, RPMI 2650 cells, SW-13 cells, T24 cells, WI-28 VA13, 2RA cells, WISH cells, BS-C-I cells, LLC-MK$_2$ cells, Clone M-3 cells, I-10 cells, RAG cells, TCMK-1 cells, Y-1 cells, LLC-PK$_1$ cells, PK(15) cells, GH$_1$ cells, GH$_3$ cells, L2 cells, LLC-RC 256 cells, MH$_1$C$_1$ cells, XC cells, MDOK cells, VSW cells, and TH-I, B1 cells, or derivatives thereof), fibroblast cells from any tissue or organ (including but not limited to heart, liver, kidney, colon, intestines, esophagus, stomach, neural tissue (brain, spinal cord), lung, vascular tissue (artery, vein, capillary), lymphoid tissue (lymph gland, adenoid, tonsil, bone marrow, and blood), spleen, and fibroblast and fibroblast-like cell lines (e.g., CHO cells, TRG-2 cells, IMR-33 cells, Don cells, GHK-21 cells, citrullinemia cells, Dempsey cells, Detroit 551 cells, Detroit 510 cells, Detroit 525 cells, Detroit 529 cells, Detroit 532 cells, Detroit 539 cells, Detroit 548 cells, Detroit 573 cells, HEL 299 cells, IMR-90 cells, MRC-5 cells, WI-38 cells, WI-26 cells, MiCl$_1$ cells, CHO cells, CV-1 cells, COS-1 cells, COS-3 cells, COS-7 cells, Vero cells, DBS-FrhL-2 cells, BALB/3T3 cells, F9 cells, SV-T2 cells, M-MSV-BALB/3T3 cells, K-BALB cells, BLO-11 cells, NOR-10 cells, C3H/IOTI/2 cells, $HSDM_1C_3$ cells, KLN205 cells, McCoy cells, Mouse L cells, Strain 2071 (Mouse L) cells, L-M strain (Mouse L) cells, L-MTK⁻ (Mouse L) cells, NCTC clones 2472 and 2555, SCC-PSA1 cells, Swiss/3T3 cells, Indian muntjac cells, SIRC cells, $C_{II}$ cells, and Jensen cells, or derivatives thereof). More preferably, the medium is used to culture mammalian cells selected from the group consisting of 293 cells, PER-C6 cells, CHO hells, COS cells and Sp2/0 cells. More preferably, the medium is used to culture 293 cells. Preferably, the medium is used to culture cells in suspension.

Cells supported by the medium of the present invention can be derived from any animal, preferably a mammal, and most preferably a mouse or a human. The cells cultivated in the present media can be normal cells or abnormal cells (i.e., transformed cells, established cells, or cells derived from diseased tissue samples).

The present invention also provides methods of cultivating mammalian epithelial or fibroblast cells using the culture medium formulations disclosed herein, comprising (a) contacting the cells with the cell culture media of the invention; and (b) cultivating the cells under conditions suitable to support cultivation of the cells. In some embodiments, the methods of the present invention can optionally include a step of contacting the cultured cells with a solution comprising one or more macromolecules (preferably comprising one or more nucleic acids) under conditions causing the introduction of one or more of the macromolecules into one or more of the cells. Preferably, cells cultivated according to these methods (which can include any of the cells described above) are cultivated in suspension.

The invention further provides compositions comprising the culture media of the present invention, which optionally can further comprise one or more mammalian epithelial or fibroblast cells, such as those described above, particularly one or more 293 embryonic kidney cells, PER-C6 retinal cells, and CHO cells.

The present invention further relates to methods of cultivating mammalian cells (particularly those described above and most particularly 293 embryonic kidney epithelial cells, PER-C6, and CHO cells) in suspension comprising (a) obtaining a mammalian cell to be cultivated in suspension; and (b) contacting the cell with the culture media of the invention under conditions sufficient to support the cultivation of the cell in suspension.

The present invention further relates to methods of producing a virus, and to viruses produced by these methods, the methods comprising (a) obtaining a mammalian cell, preferably a mammalian cell described above, e.g., a primate, especially simian and human, and most preferably a 293 embryonic kidney epithelial cell, PER-C6 cell, 911 cell, or CHO cell, to be infected with a virus; (b) contacting the cell with a virus under conditions suitable to promote the infection of the cell by the virus; and (c) cultivating the cell in the culture medium of the invention under conditions suitable to promote the production of the virus by the cell. Viruses which can be produced according to these methods include adenoviruses, adeno-associated viruses and retroviruses.

The present invention further relates to methods of producing a polypeptide, and to polypeptides produced by these methods, the methods comprising (a) obtaining a cell, preferably a mammalian cell described above and most preferably a 293 embryonic kidney epithelial cell, PER-C6, or CHO cell; (b) contacting the cell with a solution comprising a nucleic acid encoding the polypeptide under conditions causing the introduction of the nucleic acid into the cell; and (c) cultivating the cell in the culture medium of the invention under conditions favoring the expression of the desired polypeptide by the cell.

The present invention is also directed to compositions, particularly cell culture media, comprising one or more replacement compounds. In some embodiments, the replacement compounds can be metal binding compounds and/or one or more transition elements in a complex with one or more metal binding compounds. Such cell culture media of the invention can be used to grow or cultivate plant cells, animal cells (particularly human cells), insect cells, bacterial cells, yeast cells and more generally any type of eukaryotic or prokaryotic cells. Thus, the replacement compounds of the present invention can be added to any type or kind of culture media, and are preferably used to replace naturally derived metal carriers (e.g., animal derived proteins or extracts such as transferrin) in such media. The invention is also directed to methods of use of such compositions, including, for example, methods for the cultivation of eukaryotic cells, particularly animal cells, in vitro. The invention also relates to compositions comprising such culture media and one or more cells, especially those cells specifically referenced herein, and to kits comprising one or more of the above-described compositions.

In another aspect, the invention relates to a kit for the cultivation of cells in vitro. The kit comprise one or more containers, wherein a first container contains the culture medium of the present invention. The kit can further comprise one or more additional containers, each container containing one or more supplements selected from the group consisting of one or more cytokines, heparin, one or more animal or animal-derived peptides, one or more yeast peptides and one or more plant peptides (which are preferably one or more peptides from rice, aloevera, soy, maize, wheat, pea, squash, spinach, carrot, potato, sweet potato, tapioca, avocado, barley coconut and/or green bean, and/or one or more other plants).

The kit of the present invention can further comprise one or more containers comprising a nucleic acid and/or a reagent that facilitates the introduction of at least one macromolecule, e.g., a nucleic acid into cells cultured in the media of the present invention, i.e., a transfection reagent. Preferred transfection reagents include, but are not limited to, cationic lipids and the like.

A kit according to one aspect of the invention can comprise one or more of the culture media of the invention, one or more replacement compounds, which can be one or more metal binding compounds, and/or one or more transition element complexes, and can optionally comprise one or more nucleic acids and transfection reagents. Kits according to another aspect of the invention can comprise one or more cell culture media (one of which can be a basal medium) and one or more replacement compounds. Preferred replacement compounds include, but are not limited to, metal binding compounds and/or transition element complexes, said complexes comprising at least one transition element or a salt or ion thereof complexed to at least one metal-binding compound. Preferred transition elements, metal-binding compounds, and transition element complexes for use in the kits according to this aspect of the invention include those described in detail herein.

The kit of the present invention can also contain instructions for using the kit to culture cells and/or introduce macromolecules or compounds (e.g., nucleic acid, such as DNA), into cells.

It will be readily apparent to one of ordinary skill in the relevant arts that other suitable modifications and adaptations to the methods and applications described herein are obvious and can be made without departing from the scope of the invention or any embodiment thereof. Having now described the present invention in detail, the same will be more clearly understood by reference to the following examples, which are included herewith for purposes of illustration only and are not intended to be limiting of the invention.

Example 1

Semi-confluent adherent cultures of 293 Cells (ATCC, CRL 1573) are readily adapted to suspension culture. The cells are first detached with a solution of Trypsin-EDTA (0.05% Trypsin, 0.53 mM $Na_4EDTA$), and then resuspended in conventional medium supplemented with 10% FBS to inhibit the trypsin. The resuspended cells are centrifuged at 200×g for five minutes. The cell pellet is resuspended in 293 SFM (available from Invitrogen Corporation, Carlsbad, Calif.) the formulation of which is described in WO 98/08934 which is specifically incorporated herein by reference. Alternatively, the cells can be detached with VERSENE ($Na_4EDTA$, 0.53 mM) and resuspended in 293 SFM.

The initial seeding density of the 293 cells after conversion to suspension culture is $1 \times 10^6$ cells/mL. The cells are shaken on a rotary shaker at 150 rpm in a 37° C. incubator equilibrated with 8% $CO_2$-92% air. When the cells reach a density of $1.5 \times 10^6$ cells/mL they are diluted with 293 SFM to a density of $3.0 \times 10^5$ cells/mL. Because 293 cells have a tendency to aggregate, the cells can be vortexed vigorously for approximately 45 seconds to obtain a predominantly single cell suspension at the time of passaging and counting. After several passages in suspension culture, the maximum achievable density can be determined. The 293 cells which are described here were grown to approximately $3-4 \times 10^6$ cells/mL in suspension culture.

The ability of various replacement compounds to support cellular growth was evaluated using 293 cells maintained in 293 SFM (Invitrogen Corporation, Carlsbad, Calif.) without transferrin or replacement compound. Stock cultures containing 5 µg/mL human holo-transferrin were prepared in 293 SFM. For replacement compound evaluation, 293 cells were established in 125 mL shaker flasks at an initial viable seeding density of $2 \times 10^5$ cells/mL in a final volume of 20 mL. All cultures were maintained at 37° C. in humidified air containing 8% $CO_2$. To eliminate transferrin carry-over effects, cells were subcultured at 4 day intervals for a total of three passages. At each subculturing, cells were seeded at a density of $2 \times 10^5$ cells/mL. Positive control cultures contained 5 µg/mL human holo-transferrin while negative control cultures were established in the absence of either transferrin or replacement compound. Replacement compound stocks were prepared at 0.1M-0.2M in $ddH_2O$ and solubilized when necessary using 5N NaOH or HCl. Iron complexes were established using 0.2 M replacement compound and iron stocks mixed 1:1 (v/v) and incubated for 5-10 minutes at 22° C. All solutions containing replacement compounds were filter sterilized using a 0.22 µm Millex-GV filter prior to addition to transferrin and serum-free media.

Except where noted, replacement compounds were evaluated either alone or in combination with ferric chloride or ferrous sulfate at 25 µM, 50 µM and 100 µM. When used in combination, the replacement compounds were used in equimolar concentration with iron ions. Values in Table 4 represent the mean percentage of control growth for duplicate cultures determined at the third passage. Media that was not supplemented, i.e., did not contain either transferrin or replacement compound, failed to support the growth of the cells over three passages.

The results of 293 cells grown in the presence of various replacement compounds are shown in Table 4. When added to the medium formulation uncomplexed, the replacement compound is listed alone, when added as a complex with a transition metal, the source of the transition metal is listed with the replacement compound.

In this and in other examples, 293 SFM medium was used. 293 SFM medium is no longer available from Invitrogen (Carlsbad, Calif.), but similar results would be expected using 293 SFM II medium (Invitrogen, Carlsbad, Calif.).

TABLE 4

Effect of Replacement Compounds on the Growth of 293 Cells

| Replacement compound tested | Concentration | | |
|---|---|---|---|
| | 25 µM | 50 µM | 100 µM |
| 2-Hydroxypyridine-N-Oxide (293 tested at 10-50 µM) | 117 | 150 | Not Tested |
| 3-Hydroxypyridine-N-Oxide | 4 | 4 | 4 |
| 3-Hydroxypyridine-N-Oxide•Ferric Chloride | 77 | 72 | 81 |
| 3-Hydroxypyridine-N-Oxide•Ferrous Sulfate | 104 | 58 | 0 |
| Sorbitol•Ferrous Sulfate | 58 | 69 | 83 |
| Deferoxamine Mesylate•Ferric Chloride | 101 (5 µM) | 120 (10 µM) | 127 (20 µM) |
| Acetohydroxamic Acid•Ferric Chloride | 83 | 22 | 0 |
| Serine Hydroxamate•Ferric Chloride | 68 | 65 | 51 |
| Glycine•Ferric Chloride | 81 | 71 | 72 |
| Nitriloacetic Acid•Ferric Chloride | 100 | 118 | 74 |
| Nitriloacetic Acid•Ferrous Sulfate | 75 | 95 | 0 |
| 3-Hydroxy-2-Methyl-4-Pyrone (Maltol) | 0 | 28 | 81 |
| 2-Ethyl-3-Hydroxy-4-Pyrone (Ethyl Maltol) | 59 | 120 | 126 |
| 2,2-Dipyridylamine•Ferric Chloride | 118 | 96 | 101 |
| 2,2-Dipyridyl•Ferric Chloride | 51 | 96 | 0 |
| Diethylenetriamine Penta-Acetic Acid•Ferric Chloride | 79 | 96 | 102 |
| Diethylenetriamine Penta-Acetic Acid•Ferrous Sulfate | 77 | 107 | 85 |
| Nicotinic Acid-N-Oxide•Ferric Chloride | 104 | 80 | 79 |
| 2-Hydroxynicotinic Acid•Ferric Chloride (293 tested at 100, 150, 200 µM) | 0 | 0 | 99 |
| Ferrous Gluconate•Ascorbic Acid Phosphate | 86 | 109 | 101 |
| Aspartic Acid•Ferric Chloride | 81 | 86 | 100 |
| Glutamic Acid•Ferric Chloride | 102 | 68 | 83 |
| N-Acetyl-Cysteine•Ferric Chloride | 88 | 82 | 52 |
| 4-Pyridoxic Acid•Ferric Chloride | 109 | 85 | 99 |
| 2-Pyridinecarboxylic Acid•Ferrous Sulfate | 67 | 48 | 0 |
| Myo-Inositol•Ferric Chloride | 79 | 87 | 85 |
| Mimosine•Ferric Chloride | 64 | 55 | 80 |
| Ferrous Sulfate | 71 | 60 | 41 |
| Ferric Chloride | 87 | 91 | 109 |

Example 2

The ability of replacement compounds to support cellular growth in the absence of transferrin was evaluated using CHO cells maintained in CD CHO medium (Invitrogen Corporation, Carlsbad, Calif., the formulation of which is described in WO 98/08934). Stock cultures containing 5 μg/mL human holo-transferrin were prepared in CD CHO medium. For replacement compound evaluation, CHO cells were established in 125 mL shaker flasks at an initial viable seeding density of $1 \times 10^5$ cells/mL in a final volume of 20 mL. All cultures were maintained at 37° C. in humidified air containing 8% $CO_2$. To eliminate transferrin carry-over effects, cells were subcultured at 4 day intervals for a total of three passages. Positive control cultures contained 5 μg/mL human holo-transferrin while negative control cultures were established in the absence of either transferrin or replacement compound. Replacement compound stocks were prepared at 0.1M-0.2M in $ddH_2O$ and solubilized when necessary using 5N NaOH or HCl. Iron complexes were established using 0.2M replacement compound and iron stocks mixed 1:1 (v/v) and incubated for 5-10 minutes at 22° C. All solutions containing replacement compounds were filter sterilized using a 0.22 μm Millex-GV filter prior to addition to transferrin and serum-free media.

Except where noted, replacement compounds were evaluated either alone or in combination with ferric chloride or ferrous sulfate at 25 μM, 50 μM and 100 μM. Values in the table represent the mean percentage of control growth for duplicate cultures determined at the third passage. Media that was not supplemented, i.e., did not contain either transferrin or replacement compounds, failed to support the growth of the cells over three passages.

The ability of various replacement compounds to substitute for transferrin in the culture of CHO cells was determined. The results are shown in Table 5. When added to the medium formulation un-complexed, the replacement compound is listed alone, when added as a complex with a transition metal, the source of the transition metal is listed with the metal binding compound.

TABLE 5

Effect of Replacement Compounds on the Growth of CHO Cells

| Replacement compound tested | Concentration | | |
|---|---|---|---|
| | 25 μM | 50 μM | 100 μM |
| 2-Hydroxypyridine-N-Oxide | 127 | 117 | 83 |
| 3-Hydroxypyridine-N-Oxide•Ferric Chloride | 77 | 66 | 101 |
| Sorbitol•Ferric Chloride | 100 | 107 | 112 |
| Deferoxamine Mesylate•Ferric Chloride | 50 (5 μM) | 74 (10 μM) | 52 (20 μM) |
| Serine Hydroxamate•Ferric Chloride | 106 | 121 | 124 |
| Lysine•Ferric Chloride | 51 | 79 | 98 |
| Nitriloacetic Acid•Ferric Chloride | 127 | 107 | 107 |
| 2-Ethyl-3-Hydroxy-4-Pyrone | 9 | 60 | 113 |
| 2,2-Dipyridylamine•Ferric Chloride | 40 | 48 | 65 |
| Diethylenetriamine Penta-Acetic Acid•Ferrous Sulfate | 135 | 137 | 147 |
| Nicotinic Acid-N-Oxide•Ferric Chloride | 60 | 84 | 105 |
| Ferrous Gluconate•Ascorbic Acid Phosphate | 91 | 61 | 28 |
| Aspartic Acid•Ferric Chloride | 77 | 89 | 112 |
| Cysteine•Ferrous Sulfate | 83 | 64 | 45 |
| 4-Pyridoxic Acid•Ferric Chloride | 55 | 63 | 100 |
| 2-Pyridinecarboxylic Acid•Ferric Chloride | 88 | 89 | 100 |
| Kojic Acid | 0 | 0 | 0 |
| Kojic Acid•Ferric Chloride | 89 | 88 | 85 |
| 2,3-Dihydrobenzoic Acid•Ferric Chloride | 71 | 0 | 0 |
| Ferrous Sulfate | 88 | 79 | 38 |
| Ferric Chloride | 56 | 85 | 101 |

Example 3

The ability of replacement compounds to support cellular growth in the absence of transferrin was evaluated using Sp2/0 cells maintained in CD Hybridoma medium (Invitrogen Corporation, Carlsbad, Calif.).

Stock cultures containing 5 μg/mL human holo-transferrin were prepared in CD Hybridoma medium. For replacement compound evaluation, Sp2/0 cells were established at an initial viable cell density of $0.5 \times 10^5$ cells/mL in stationary culture using 75 $cm^2$ tissue culture flasks in a final volume of 20 mL. All cultures were maintained at 37° C. in humidified air containing 8% $CO_2$. To eliminate transferrin carry-over effects, cells were subcultured at the same seeding density at 4 day intervals for a total of three passages. Positive control cultures contained 5 μg/mL human holo-transferrin while negative control cultures were established in the absence of either transferrin or replacement compound. Replacement compound stocks were prepared at 0.1M-0.2M in $ddH_2O$ and solubilized when necessary using 5N NaOH or HCl. Iron complexes were established using 0.2M replacement compound and iron stocks mixed 1:1 (v/v) and incubated for 5-10 minutes at 22° C. All solutions containing replacement compounds were filter sterilized using a 0.22 μm Millex-GV filter prior to addition to transferrin and serum-free media.

Except where otherwise noted, replacement compounds were evaluated either alone or in combination with ferric chloride or ferrous sulfate at 25 μM, 50 μM and 100 μM. Values in the table represent the mean percentage of control growth for duplicate cultures determined at the third passage. Media that was not supplemented, i.e., did not contain either transferrin or replacement compounds, failed to support the growth of the cells over three passages.

The ability of various replacement compounds to substitute for transferrin in the culture of Sp2/0 cells was determined and the results are seen in Table 6. When added to the medium formulation un-complexed, the replacement compound is listed alone, when added as a complex with a transition metal, the source of the transition metal is listed with the replacement compound.

TABLE 6

Effect of Replacement Compounds on the Growth of Sp2/0 Cells

| Replacement compound tested | Concentration | | |
|---|---|---|---|
| | 25 μM | 50 μM | 100 μM |
| 2-Hydroxypyridine-N-Oxide | 98 | 93 | 89 |
| 3-Hydroxypyridine-N-Oxide•Ferric Chloride | 55 | 54 | 57 |
| Sorbitol•Ferric Chloride | 94 | 55 | 60 |

TABLE 6-continued

Effect of Replacement Compounds on the Growth of Sp2/0 Cells

| Replacement compound tested | Concentration | | |
|---|---|---|---|
| | 25 µM | 50 µM | 100 µM |
| Deferoxamine Mesylate•Ferric Chloride (All lines tested at 5, 10, 20 µM) | 0 (5 µM) | 0 (10 µM) | 0 (20 µM) |
| Acetohydroxamic Acid•Ferric Chloride (Sp2 tested at 5, 10, 20 µM) | 40 | 48 | 47 |
| Serine Hydroxamate•Ferric Chloride | 46 | 66 | 62 |
| Glycine•Ferric Chloride | 34 | 61 | 56 |
| Nitriloacetic Acid•Ferric Chloride | 88 | 87 | 70 |
| Nitriloacetic Acid | 0 | 0 | 0 |
| 3-Hydroxy-2-Methyl-4-Pyrone (Maltol) | 0 | 0 | 0 |
| 3-Hydroxy-2-Methyl-4-Pyrone•Ferric Chloride | 60 | 71 | 75 |
| 2-Ethyl-3-Hydroxy-4-Pyrone (Ethyl Maltol) | 0 | 75 | 116 |
| Diethylenetriamine Penta-Acetic Acid•Ferrous Sulfate | 54 | 90 | 91 |
| 2-Hydroxynicotinic Acid•Ferric Chloride) | 64 | 82 | 85 |
| Ferrous Gluconate•Ascorbic Acid Phosphate | 92 | 94 | 93 |
| Glutamine•Ferric Chloride | 36 | 55 | 65 |
| Asparagine•Ferric Chloride | 36 | 51 | 54 |
| Cysteine•Ferrous Sulfate | 85 | 79 | 67 |
| 4-Pyridoxic Acid•Ferric Chloride | 40 | 73 | 76 |
| 2-Pyridinecarboxylic Acid•Ferric Chloride | 0 | 30 | 48 |
| Morpholine•Ferric Chloride | 54 | 64 | 81 |
| 3-Hydroxy-2-Nitropyridine•Ferric Chloride | 52 | 62 | 72 |
| Kojic Acid | 0 | 0 | 0 |
| Kojic Acid•Ferric Chloride | 0 | 0 | 0 |
| Ferrous Sulfate | 91 | 103 | 94 |
| Ferric Chloride | 55 | 73 | 74 |

Example 4

Protocol Used for Transfections

Cells used were 293-F cells cultured either in suspension or attached. 293-F cells are a clone of 293 cells obtained from Robert Horlick at Pharmacopeia, Princeton, N.J. Cells were adapted to the test media for several passages (>4) prior to transfection experiments. When cultured in suspension, cells were split to $3 \times 10^5$ viable cells per ml at each passage. On the week of transfection cells were seeded at $3 \times 10^5$ viable cells per ml. After ~48 hrs of growth (day 2) cells were vortexed for 30 seconds and counted and appropriate volumes used for transfection as described in procedures below.

The composition of the base media used for the transfection experiments is shown in Table 7.

TABLE 7

| GP | COMP ID# | COMPONENTS | GM/100 L | GM/L |
|---|---|---|---|---|
| 1 | 8101009 | L-Arginine HCl | 43 | 0.430 |
| 1 | 8101013 | L-Asparagine Anhyd | 2.64 | 0.026 |
| 1 | 8101016 | L-Aspartic Acid | 7.5 | 0.075 |
| 1 | 8101035 | L-Cysteine HCl H2O | 7.5 | 0.075 |
| 1 | 8101048 | L-Glutamic Acid | 2.94 | 0.029 |
| 1 | 8101062 | L-Histidine HCl H2O | 5.7 | 0.057 |
| 1 | 8101072 | L-Isoleucine | 19 | 0.190 |
| 1 | 8101077 | L-Leucine | 28 | 0.280 |
| 1 | 8101083 | L-Lysine HCl | 25.5 | 0.255 |
| 1 | 8101086 | L-Methionine | 11.5 | 0.115 |

TABLE 7-continued

| GP | COMP ID# | COMPONENTS | GM/100 L | GM/L |
|---|---|---|---|---|
| 1 | 8101095 | L-Phenylalanine | 7 | 0.070 |
| 1 | 8101101 | L-Serine | 25 | 0.250 |
| 1 | 8101104 | L-Threonine | 6 | 0.060 |
| 1 | 8101110 | L-Tryptophan | 2 | 0.020 |
| 1 | 8101116 | L-Valine | 19 | 0.190 |
| 1 | 8801985 | L-Tyrosine Disodium Salt | 10 | 0.100 |
| 2 | 8205023 | D-Glucose (Dextrose) | 200 | 2.00 |
| 2 | 8503100 | Vitamin B12 | 0.103 | 0.0010 |
| 2 | 8503140 | Biotin | 0.0097 | 0.000097 |
| 2 | 8503200 | Choline Chloride | 1.4 | 0.014 |
| 2 | 8503370 | Folic Acid | 0.5 | 0.005 |
| 2 | 8503390 | i-Inositol | 1.8 | 0.018 |
| 2 | 8503450 | Niacinamide | 0.122 | 0.0012 |
| 2 | 8503460 | D Calcium Pantothenate | 0.119 | 0.0012 |
| 2 | 8503510 | Pyridoxine HCl | 0.103 | 0.0010 |
| 2 | 8503520 | Riboflavin | 0.022 | 0.0002 |
| 2 | 8503540 | Thiamine HCl | 0.112 | 0.0011 |
| 2 | 8800517 | Ethanolamine HCl | 0.5 | 0.005 |
| 2 | 8801680 | Putrescine 2HCl | 0.016 | 0.0002 |
| 2 | 8901840 | Sodium Pyruvate | 11 | 0.110 |
| 3 | 8205023 | D-Glucose (Dextrose) | 200 | 2.00 |
| 3 | 8503560 | DL Lipoic Acid Thioctic (see Step 1 process instruction below) | 0.2 | 0.0020 |
| 3 | 8801225 | Linoleic Acid (see Step 1 process instruction below) | 0.006 | |
| 4 | 0855845 | Opti-MEM (100000X) TES | 1 | 0.010 |
| 4 | 8800615 | Ferric Nitrate 9H2O (see Step 2 process instruction below) | 0.081 | 0.0008 |
| 4 | 8801314 | Magnesium Chloride Anhyd | 7.62 | 0.076 |
| 4 | 8801340 | Magnesium Sulfate Anhyd | 2.41 | 0.024 |
| 4 | 8801635 | Potassium Chloride | 27.6 | 0.276 |
| 4 | 8802626 | Zinc Sulfate H2O (see Step 2 process instruction below) | 0.00874 | |
| 4 | 8951830 | Sodium Chloride | 441 | 4.41 |
| 4 | 8951837 | Sodium Phosphate Monobasic H2O | 12.5 | 0.125 |
| 5 | 8800320 | Calcium Chloride Anhyd | 1.47 | 0.015 |
| 6 | 8205023 | D-Glucose (Dextrose) | 50 | 0.500 |
| 6 | 8701160 | Phenol Red | 0.1 | 0.0010 |

In addition, the base media comprises 2.4 g/L NaHCO$_3$, 2.98 g/L Hepes, 4 mM L-glutamine and 3 ml/L PLURONIC F-68 (Invitrogen Corp., Carlsbad, Calif.).

The osmolarity is adjusted to from about 275-310 mOsm, preferably about 280 mOsm and the pH is adjusted to from about 7.0 to about 7.45 preferably about 7.4 respectively. The above media is referred to as 293 SFM w/o insulin, w/o transferrin, w/o citrate chelate, w/o dextran sulfate, with L-glutamine and with PLURONIC F-68. To that media, one or more of the replacement compounds of the invention and one or more metals can be added, for example, 25 µM 2-hydroxypyridine-N-oxide and 0.375 mg/L ZnSO$_4$.7H$_2$O can be added for the transfection media.

For transfection experiments in 15 ml shaker flasks, a volume of cells corresponding to $1.5 \times 10^7$ viable cells was centrifuged and the supernatant was removed. The pellets were suspended in 14.5 ml fresh test media. Each medium was tested in duplicate.

The nucleic acid was prepared for transfection by combining 700 test media+60 µl DNA (the DNA used was plasmid pCMV-SPORT-β-gal available from Invitrogen Corporation, Carlsbad, Calif. Cat#10586-014)+240 µl LIPOFECTAMINE 2000 (available from Invitrogen Corporation, Carlsbad, Calif. Cat #11668-019) in a microfuge tube and incubating the mixture for 30 minutes at room temperature in order to form complexes of nucleic acid and transfection reagent. In this and all subsequent experiments, when complexing DNA and lipid for transfections, the additions were always done by first adding the DNA to the tested media, then adding the LIPOFECTAMINE 2000 to the DNA-tested media mix. After complex formation, 500 µl of the complex was added to each of the duplicate shaker flasks. The final cell concentration was $1 \times 10^6$ viable cells per ml, the final DNA concentration was 1 µg per $1 \times 10^6$ viable cells and the final LIPOFECTAMINE 2000 concentration was 8 µl per $1 \times 10^6$ viable cells.

When 10 ml shaker flasks were used, a volume of cells corresponding to $1.0 \times 10^7$ viable cells was centrifuged and the supernatant was removed. The pellets were re-suspended in 9.5 ml fresh test media. In a microfuge tube 800 µl test media+40 µl DNA+160 µl LIPOFECTAMINE 2000 were combined and incubated for 30 minutes to permit complex formation and 500 µl of the complex added to each of the shaker flasks. The final cell concentration in the suspension in the shaker flasks was $1 \times 10^6$ viable cells per ml, the final DNA concentration was 1 µg per $1 \times 10^6$ viable cells and the final LIPOFECTAMINE 2000 concentration was 8 µl per $1 \times 10^6$ viable cells.

After 24 hrs, 2 ml samples were removed and the β-galactosidase activity determined. Each 2 ml sample was centrifuged, the supernatant removed and the pelleted cells were re-suspended pellets in 1 ml of Dulbecco's-PBS (D-PBS, Invitrogen Corporation, Carlsbad, Calif.). The cells were then centrifuged and re-suspended a second time in 1 ml of D-PBS. The samples were stored at −70° C. Prior to the assay for β-galactosidase, samples were subjected to cycles of freezing and thawing a total of five times. Due to the high amounts of β-galactosidase activity, 10 µl and 20 µl samples were run against a standard curve ranging from 0-700 ng β-galactosidase.

For determination of β-galactosidase activity by in situ staining, 1 ml samples (i.e., $\sim 1 \times 10^6$ cells) were used.

Protocol Used to Transfect 293-F Cells in 24-Well Plates:

Three wells were set up for each treatment. A volume of media corresponding to $3 \times 10^6$ viable cells was centrifuged. The supernatant was removed and the cells re-suspended in 600 µl test media. Each well of a 24 well plate received 200 µl of the re-suspended cells.

To prepare the nucleic acid for the transfection experiments, 93 µl test media+3 µl DNA+24 µl LIPOFECTAMINE 2000 were combined in a microfuge tube and complexed for 30 minutes. A 40 µl aliquot of complex was added to each well. 250 µl test media was added to each well five hours after addition of complex. The final cell concentration was $1 \times 10^6$ viable cells per well; the final DNA concentration was 1 µg per $1 \times 10^6$ viable cells and the final LIPOFECTAMINE 2000 concentration was 8 µl per $1 \times 10^6$ viable cells.

24 hrs post-transfection, samples were collected for β-galactosidase quantitation. The contents of duplicate wells were pooled (i.e. $\sim 2 \times 10^6$ cells for the assay) for each sample and transferred to a microfuge tube. The cells were centrifuged, the supernatant was removed and the cells were re-suspended in 1 ml of D-PBS. The cells were pelleted a second time and re-suspended in 1 ml of D-PBS. The samples were then stored at −70° C. Prior to the assay for β-galactosidase, samples were freeze-thawed a total of five times. Aliquots (15 µl and 25 µl) of each sample were assayed and the activity determined by comparison to a standard curve ranging from 0-70 ng β-galactosidase.

The third well of each treatment was used for in situ staining for β-galactosidase activity (i.e., $\sim 1 \times 10^6$ cells).

Example 5

Comparison of Transfection Efficiencies of Cells Grown in the Presence of Various Replacement Compounds 293 cells were grown in monolayer culture in the presence of the various replacement compounds indicated and transfection experiments performed as described above. The results are shown in Table 8 and the values are β-galactosidase activity expressed as nanograms of β-galactosidase per $2 \times 10^6$ cells. A comparison was made between the transfection efficiency of DNA complexes formed in D-MEM medium and DNA complexes formed in test medium. The replacement compounds were present at a concentration of 25 µM.

TABLE 8

| ID | Replacement compound in test media: | D-MEM used for complexing, Test media to re-suspend cells | Test Media used for complexing and to re-suspend cells |
|---|---|---|---|
| A | Human Transferrin (as control) | 326 | 3279 |
| B | 2-hydroxypyridine-N-oxide | 354 | 1314 |
| C | 3-hydroxypyridine-N-Oxide•Ferrous sulfate | 176 | 317 |
| D | Deferoxamine Mesylate•Ferric Chloride | 154 | 301 |
| E | 2-ethyl-3-hydroxy-4-pyrone (ethyl maltol) | 378 | 1827 |
| F | 2,2-dipyridylamine•ferric chloride | 347 | 459 |
| G | Diethylene-triamine-penta acetic acid•Ferric chloride | 131 | 574 |
| H | Diethylene-triamine-penta acetic acid•Ferrous sulfate | 234 | 720 |
| I | Ferrous Gluconate•Ascorbic Acid | 116 | 275 |
| J | Ferric Chloride | 18 | 0 |
| K | 2-methyl-3-hydroxy-4-pyrone | 103 | 52 |
| L | Nitrilotriacetic acid•ferric chloride | 45 | 33 |
| M | Ferrous sulfate | 258 | 406 |
| Stock (293-II) | Stock (293 SFM II medium) | 3 | 0 |
| D-MEM + 10% FBS | D-MEM +10% FBS + 0.1 mM NEAA | 1054 | 1464 |

Transfection efficiency was generally better when test media rather than D-MEM was used for complexing the DNA and lipid. The transferrin control (ID#A) worked best, reflecting that transferrin facilitates transfections. It should also be noted that cell growth in the above test media was comparable to growth in media containing transferrin and to growth in 293SFM-II.

Base media for test media was 293-II+insulin+L-glutamine+PLURONIC F-68 (−) dextran sulfate (−) transferrin (+) replacement compound (A-M for test media, see table).

Example 6

Effect of Varying Concentration of Replacement Compound and Effect of Media Used to Form Nucleic Acid Complexes 293 cells were grown in monolayer culture in base medium supplemented with the indicated replacement compounds at the concentrations specified in Table 9. The top number in the concentration column is the concentration of the first supplement and the second number in the concentration column is the concentration of the second supplement. The effects of the medium used to form DNA complexes were tested. The results are presented as nanograms of β-galactosidase per $2 \times 10^6$ cells.

TABLE 9

| ID | Compound added to base media | Concentration added | D-MEM used for complexing, Test media to re-suspend cells | Test Media used for complexing and to re-suspend cells |
|---|---|---|---|---|
| A | + Human Transferrin (as control)<br>+ Insulin | 5 μg/ml<br>10 μg/ml | 401 | 550 |
| B | + 2-ethyl-3-hydroxy-4-pyrone (ethyl maltol)<br>+ insulin | 50 μM<br>10 μg/ml | 245 | 997 |
| C | + 2-ethyl-3-hydroxy-4-pyrone (ethyl maltol)<br>+ insulin | 100 μM<br>10 μg/ml | Discontinued at p1 of adaptation to media due to v. poor growth | |
| D | + 2-hydroxypyridine-N-oxide<br>+ insulin | 25 μM<br>10 μg/ml | 361 | 2054 |
| E | + 2-hydroxypyridine-N-oxide<br>+ insulin | 50 μM<br>10 μg/ml | Discontinued at p1 of adaptation to media due to v. poor growth | |
| F | + Diethylene-triamine-penta acetic acid•Ferrous sulfate (DPTA•FeSO4)<br>+ insulin | 50 μM<br>10 μg/ml | 262 | 1029 |
| G | + Transferrin<br>+ ZnSO4 | 5 μg/ml<br>0.375 μg/ml | 635 | 1700 |
| H | + 2-ethyl-3-hydroxy-4-pyrone (ethyl maltol)<br>+ ZnSO4 | 50 μM<br>0.375 μg/ml | 242 | 395 |
| I | + 2-ethyl-3-hydroxy-4-pyrone (ethyl maltol)<br>+ ZnSO4 | 100 μM<br>0.375 ug/ml | Discontinued at p1 of adaptation to media due to v. poor growth | |
| J | + 2-hydroxypyridine-N-oxide<br>+ ZnSO4 | 25 μM<br>0.375 μg/ml | 1066 | 2937 |
| K | + 2-hydroxypyridine-N-oxide<br>+ ZnSO4 | 50 μM<br>0.375 μg/ml | Discontinued at p1 of adaptation to media due to v. poor growth | |
| L | + Diethylene-triamine-penta acetic acid•Ferrous sulfate (DPTA•FeSO4)<br>+ ZnSO4 | 50 μM<br>0.375 μg/ml | 378 | 2372 |
| M | + 2-ethyl-3-hydroxy-4-pyrone (ethyl maltol)<br>+ ZnSO4 | 50 μM<br>0.188 μg/ml | 94 | 218 |
| N | + 2-ethyl-3-hydroxy-4-pyrone (ethyl maltol)<br>+ ZnSO4 | 50 μM<br>0.750 μg/ml | 482 | 624 |
| O | + 2-ethyl-3-hydroxy-4-pyrone (ethyl maltol)<br>+ ZnSO4<br>+ CaCl2 | 50 μM<br>0.375 μg/ml<br>0.1 mg/ml | Discontinued at p1 of adaptation to media due to v. poor growth | |
| P | + 2-ethyl-3-hydroxy-4-pyrone (ethyl maltol)<br>+ insulin | 25 μM<br>10 μg/ml | 220 | 282 |
| Q | + 2-ethyl-3-hydroxy-4-pyrone (ethyl maltol)<br>+ ZnSO4 | 25 μM<br>0.375 μg/ml | 142 | 484 |
| | Stock in 293SFM II (Catalogue) | | 0 | 0 |
| | D-MEM + 10% FBS | | Out of range, too high* | Out of range, too high* |

*Note:
there were only about $1 \times 10^6$ viable cells/2-wells in the wells for cells grown in D-MEM + 10% FBS vs. $2 \times 10^6$ viable cells/2-wells for all other samples.

Ethyl maltol did not support growth at 100 μM. Growth in 50 μM was a little better than 25 μM but better for transfection in the presence of insulin (ID#B, C, H, P and Q) and about the same in presence of ZnSO4.

2-hydroxypyridine did not support growth at 50 Transfection was better when this chelate was present in combination with ZnSO4 instead of insulin (see ID#D, E and J).

DPTA.FeSO$_4$ supported growth better in the presence of insulin than in the presence of ZnSO$_4$, however, growth was acceptable in the presence of ZnSO$_4$. Transfection results were much better when the chelate was present in combination with ZnSO$_4$ instead of insulin (see ID#F and L).

Example 7

Effect of Zinc Sulfate Concentration on Transfection Efficiency of Attached Cells The transfection efficiency of cells grown in the presence of ZnSO$_4$+ chelating agent as a replacement for insulin was tested at various concentrations of chelator and ZnSO$_4$ and the results are shown in Table 10. Cells were prepared in monolayer culture in base medium containing the indicated supplements and transfected and assayed as described above.

TABLE 10

| ID | Compound added to base media | Concentration added | β-gal expression (ng/~2 × 10$^6$ cells) | X-gal stain % transfection efficiency |
|---|---|---|---|---|
| A | + Human Transferrin (as control) | 5 μg/ml | 1495 | ~50-60 |
|   | + Insulin | 10 μg/ml | | |
| B | + 2-ethyl-3-hydroxy-4-pyrone (ethyl maltol) | 50 μM | 1106 | ~50-60 |
|   | + insulin | 10 μg/ml | | |
| C | +2-ethyl-3-hydroxy-4-pyrone (ethyl maltol) | 50 μM | 1157 | ~40 |
|   | + ZnSO4 (1x) | 0.375 μg/ml | | |
| D | + 2-ethyl-3-hydroxy-4-pyrone (ethyl maltol) | 50 μM | 570 | N/A |
|   | + ZnSO4 (2x) | 0.750 μg/ml | | |
| E | + 2-ethyl-3-hydroxy-4-pyrone (ethyl maltol) | 50 μM | 210 | N/A |
|   | + ZnSO4 (5x) | 1.875 μg/ml | | |
| F | + 2-hydroxypyridine-N-oxide | 25 μM | 1089 | N/A |
|   | + insulin | 10 μg/ml | | |
| G | + 2-hydroxypyridine-N-oxide | 25 μM | Discontinued at p3 of adaptation due to poor growth | |
|   | + ZnSO4 (0.5x) | 0.188 μg/ml | | |
| H | + 2-hydroxypyridine-N-oxide | 25 μM | 1531 | ~85-95 |
|   | + ZnSO4 (1x) | 0.375 μg/ml | | |
| I | + 2-hydroxypyridine-N-oxide | 25 μM | 1540 | N/A |
|   | + ZnSO4 (2x) | 0.750 μg/ml | | |
| J | + 2-hydroxypyridine-N-oxide | 25 μM | 1474 | N/A |
|   | + ZnSO4 (5x) | 1.875 μg/ml | | |
| K | + 2-hydroxypyridine-N-oxide | 10 μM | 1285 | N/A |
|   | + ZnSO4 (1x) | 0.375 μg/ml | | |
| L | + Diethylene-triamine-penta acetic acid•Ferrous sulfate | 50 μM | Discontinued at p3 of adaptation due to poor growth | |
|   | + insulin | 10 μg/ml | | |
| M | + Diethylene-triamine-penta acetic acid•Ferrous sulfate | 50 μM | Discontinued at p3 of adaptation due to poor growth | |
|   | + ZnSO4 (0.5x) | 0.188 μg/ml | | |
| N | + Diethylene-triamine-penta acetic acid•Ferrous sulfate | 50 μM | 836 | ~50 |
|   | + ZnSO4 (1x) | 0.375 μg/ml | | |
| O | + Diethylene-triamine-penta acetic acid•Ferrous sulfate | 50 μM | 710 | N/A |
|   | + ZnSO4 (2x) | 0.750 μg/ml | | |
| P | + Diethylene-triamine-penta acetic acid•Ferrous sulfate | 50 μM | 467 | N/A |
|   | + ZnSO4 (5x) | 1.875 μg/ml | | |
| Q | + Human Transferrin | 5 μg/ml | 766 | N/A |
|   | + ZnSO4 (1x) | 0.375 μg/ml | | |
| Cat. | Catalog 293 SFM II | | 0 | N/A |
| D-Mem | D-MEM + 10% FBS + 0.1 mM NEAA | | Out of range (too high >5000 | ~85-95 |

Ethyl Maltol (samples B-E) supported growth at all concentrations of ZnSO$_4$ tested (1×=0.188 μg/ml, 2×=0.375 μg/ml and 5×=1.875 μg/ml); however, expression decreased with increase in ZnSO$_4$ concentration (see C, D and E) with 1× ZnSO$_4$ being the best. X-gal staining showed a transfection efficiency of ~40% in media with 1× ZnSO$_4$ and of ~50-60% in media with insulin.

2-hydroxypyridine at a concentration of 25 μM (samples F-J) supported growth at concentrations of 1×, 2× and 5× ZnSO$_4$, but not at 0.5×. Expression was about the same at 1×, 2× and 5× ZnSO$_4$ (see H, I, and J). X-gal staining was only done on sample H (1× ZnSO$_4$) and showed a transfection efficiency at 85-95%.

2-hydroxypyridine at a concentration of 10 μM (sample K) supported growth in combination with 1× ZnSO$_4$. Expression was slightly lower than when 2-hydroxypyridine is at 25 μM (compare H to K).

DPTA.FeSO$_4$ supported growth at concentrations of 1×, 2× and 5× ZnSO$_4$, but not at 0.5×. Expression decreased with increasing concentrations of ZnSO$_4$, with 1× being the best. X-gal staining showed a transfection efficiency of ~50% (ID#N).

Cells in D-MEM+10% FBS+0.1 mM NEAA had very high expression which was out of the range of the standard curve and estimated at >5000 ng/~2×10$^6$ cells. X-gal staining showed transfection efficiency to be at about 85-95%.

Cells in all test media were very clumped both at 5 hrs post transfection (right before feeding) and at 24 hrs (prior to collection). Cells in catalog control were not clumped and uniformly covered the bottom of the well. Also, the amount of cells appeared to be too many for the well resulting in cells sitting on top of each other in several layers.

Example 8

Effect of Varying Zinc Sulfate Concentration in the Presence of 2-Hydroxypyridine-N-Oxide 293 cells were grown in monolayer culture in base medium in the presence of the indicated supplements. The cells were transfected and assayed as above. The results are shown in Table 11.

TABLE 11

| ID | Compound added to base media | Concentration added | β-gal expression (ng/~2 × 10$^6$ cells) |
|---|---|---|---|
| H | + 2-hydroxypyridine-N-oxide | 25 μM | 1671 |
|   | + ZnSO$_4$ (1x) | 0.375 μg/ml | |
| I | + 2-hydroxypyridine-N-oxide | 25 μM | 1844 |
|   | + ZnSO$_4$ (2x) | 0.750 μg/ml | |
| J | + 2-hydroxypyridine-N-oxide | 25 μM | 2933 |
|   | + ZnSO$_4$ (5x) | 1.875 μg/ml | |

TABLE 11-continued

| ID | Compound added to base media | Concentration added | β-gal expression (ng/~2 × 10⁶ cells) |
|---|---|---|---|
| K | + 2-hydroxypyridine-N-oxide + ZnSO₄ (1x) | 10 μM 0.375 μg/ml | 2258 |
| 8E5 | 8 × 10⁵ cells/well in media H above | | 1607* |
| 6E5 | 6 × 10⁵ cells/well in media H above | | 1290* |
| 4E5 | 4 × 10⁵ cells/well in media H above | | 462* |
| 2E5 | 2 × 10⁵ cells/well in media H above | | 0* |
| R-H | Same as H above, but on rotator | | 1138* |
| R-6E5 | Same as 6E5 above but on rotator | | 1143* |

*Values are the total nanograms of β-galactosidase produced by two wells, each well set up at the concentration of cells indicated. For example, for 8E5, the number is the nanograms of β-galactosidase produced by two wells at 8 × 10⁵ cells/well, i.e., 1607 ng/~1.6 × 10⁶ cells.

Continuous rotation of cells during the transfection did not improve transfection results.

Increasing concentrations of ZnSO₄ seemed to increase expression. This is in contrast to the results present in the preceding example where additional ZnSO₄ did not seem to affect expression levels.

Lower concentration of 2-hydroxypyridine (10 μM) increases expression (compare H to K). Again, this was not seen in the last experiment were K was actually a little lower than H.

Example 9

Comparison of Transfection Efficiencies for Nucleic Acids Complexed in D-PBS and Media of the Present Invention 293 cells were grown in monolayer culture in base media supplemented with the indicated chelator and metal salt at the indicated concentrations. The concentration of the chelator is given in μmoles/l and the concentration of the metal salt is given in μgrams/ml. For comparison, a 10 ml flask of 293 cells in suspension culture in test media supplemented with +2-hydroxypyridine-N-oxide at 25 μM and ZnSO₄ at 0.375 μg/ml was transfected. The concentration of the cells in the media was 1×10⁶ cell/ml, the concentration of DNA used was 1 μg DNA/10⁶ cells, the concentration of LIPOFECTAMINE 2000 used was 8 μl/10⁶ cells. The results are shown in Table 12.

TABLE 12

| ID | Compound added to base media | Concentration added | Exp. A complex & resuspend in test media | Exp. B complex in D-PBS & resuspend in test media | Exp. C complex & resuspend in test media |
|---|---|---|---|---|---|
| A | + 2-hydroxypyridine-N-oxide + ZnSO4 (1x) | 25 μM 0.375 μg/ml | 913 | 159 | |
| B | + 2-hydroxypyridine-N-oxide + ZnSO4 (2x) | 25 μM 0.750 μg/ml | 732 | 221 | |
| C | + 2-hydroxypyridine-N-oxide + ZnSO4 (5x) | 25 μM 1.875 μg/ml | 1054 | 262 | |
| D | + 2-hydroxypyridine-N-oxide + ZnSO4 (1x) | 10 μM 0.375 μg/ml | 738 | 123 | |
| E | + 2-hydroxypyridine-N-oxide + ZnSO4 (2x) | 10 μM 0.750 μg/ml | 569 | 92 | |
| F | + 2-hydroxypyridine-N-oxide + ZnSO4 (5x) | 10 μM 1.875 μg/ml | 624 | 78 | |
| G | + 2-hydroxypyridine-N-oxide + ZnSO4 (1x) | 5 μM 0.375 μg/ml | 536 | 291 | |
| Flask | + 2-hydroxypyridine-N-oxide + ZnSO4 (1x) | 25 μM 0.375 μg/ml | | | 29118 |

In situ staining for β-galactosidase was done and showed that D-PBS should not be used for complexing, as efficiencies were less than or equal to 20%. Transformation efficiencies of the samples transfected with DNA complexed in test media were in the range of 50-85% transfected. The best efficiency seen so far was in the cells from the shaker flask at 98-100% transfection efficiency.

β-galactosidase expression was lower overall than in previous experiments but the trend seems similar. Again the data show that D-PBS should not be used for complexing in these experiments. The β-galactosidase expression in the cells in suspension culture in shaker flasks was substantially higher than that seen in monolayer culture. It should be emphasized that the flask was put on a shaker platform (125 rpm) from the time of transfection to the time of collection 24 hrs later. The improved transfection and resulting expression can be due to the cells being in better shape in the shaker flask than in the 24-well plates over the incubation period.

Example 10

Effects of Varying Zinc Sulfate and 2-Hydroxypyridine-N-Oxide Concentrations on Transfection Efficiencies of Cells in Suspension A comparison of transfection results obtained with 293 cells in suspension culture versus monolayer culture was performed. Cells in test media A were transfected in a 15 ml volume and cells in test media B-F were transfected in 10 ml volume. All cell densities were $1 \times 10^6$ viable cells per ml at transfection set-up. DNA and lipid concentrations used were 1 µg DNA and 8 µl LIPOFECTAMINE 2000 per $1 \times 10^6$ viable cells. Duplicate samples of cells in test media A were transfected and the results from both replicates are shown in table 13.

TABLE 13

| ID | Compound added to base media | Concentration added | β-gal expression (ng/ ~2 × 10⁶ cells) | X-gal stain % transfection efficiency |
|---|---|---|---|---|
| A | + 2-hydroxypyridine-N-oxide | 25 µM | 17218 | 96 |
|   | + ZnSO4 (1x) | 0.375 µg/ml | 15283 | 98 |
| B | + 2-hydroxypyridine-N-oxide | 25 µM | 29335 | 99 |
|   | + ZnSO4 (2x) | 0.750 µg/ml | | |
| C | + 2-hydroxypyridine-N-oxide | 25 µM | 28972 | 99 |
|   | + ZnSO4 (5x) | 1.875 µg/ml | | |
| D | + 2-hydroxypyridine-N-oxide | 10 µM | 25018 | 99 |
|   | + ZnSO4 (1x) | 0.375 µg/ml | | |
| E | + 2-hydroxypyridine-N-oxide | 10 µM | 23319 | 98 |
|   | + ZnSO4 (2x) | 0.750 µg/ml | | |
| F | + 2-hydroxypyridine-N-oxide | 10 µM | 25991 | 95 |
|   | + ZnSO4 (5x) | 1.875 µg/ml | | |

For cells transfected in 24-well plates, cells densities used were $1 \times 10^6$ viable cells per well. DNA and lipid concentrations used were 1 µg DNA and 8 µl LIPOFECTAMINE 2000 per $1 \times 10^6$ viable cells and the results are shown in Table 14.

TABLE 14

| ID | Compound added to base media | Concentration added | β-gal expression (ng/ ~2 × 10⁶ cells) | X-gal stain % transfection efficiency |
|---|---|---|---|---|
| A | + 2-hydroxypyridine-N-oxide | 25 µM | 1374 | 10 |
|   | + ZnSO4 (1x) | 0.375 µg/ml | | |
| B | + 2-hydroxypyridine-N-oxide | 25 µM | 1240 | 20 |
|   | + ZnSO4 (2x) | 0.750 µg/ml | | |
| C | + 2-hydroxypyridine-N-oxide | 25 µM | 1357 | 60 |
|   | + ZnSO4 (5x) | 1.875 µg/ml | | |

Transfection efficiencies and β-galactosidase expression levels were much better when transfections were done in shaker flasks at 125 rpm rather than in stationary plates.

Expression in media A was lower than in the previous experiments where expression was 29118 ng/~$2 \times 10^6$ cells. The volume used in that experiment was 10 ml in a 125 ml shaker flask. Growth data for the adaptation of the cells to the test media shows that cells densities are similar for all media A-F. X-gal staining of cells shows similar transfection efficiencies.

Example 11

Comparison of the Growth of Cells in Transfection Media

Frozen aliquots of 293-F cells and 293-H cells were thawed and suspended in 293 SFM II (Invitrogen Corporation, Carlsbad, Calif.) for 1 passage before being counted and suspended at a concentration $3 \times 10^5$ viable cells/ml in test media.

The cells were suspended in 15 ml of test media in a 125 ml shaker flask. The cells were shaken at 125 rpm on a rotary shaker in an atmosphere of 8% $CO_2$/92% air. The compositions of media A, B and C were as shown in Table 14; catalog media was 293 SFM II (Invitrogen Corporation, Carlsbad, Calif.). Cells were counted every four days and split to $3 \times 10^5$ viable cells/ml at that time. FIGS. 1A and 1B show the cell density at each of the first 3 passages in the test media. FIG. 1A shows the cell densities of the 293-F cells while FIG. 1B shows the densities of the 293-H cells The 293-F cells adapted well into the test media. There was some clumping but vortexing was enough to get a single cell suspension.

The 293-H cells grew to similar densities in the test media as in the 293SFM II. However, there was a lot of clumping that could not be resolved by vortexing.

In FIGS. 2A and 2B, a growth curve comparing the growth of 293-F&H cells in a single passage is shown. 25 ml cultures in 125 ml flasks were seeded with $3 \times 10^5$ viable cells/ml in triplicate and 1 ml aliquots were taken each day and the viable cells counted. Catalog media was 293 SFM II supplemented with 4 mM glutamine and test media A, B and C were as in Table 14. FIG. 2A shows the results obtained with 293-F cells and FIG. 2B shows the results obtained with 293-H cells. In all cases, the test media supported cell growth more effectively than the catalog media.

Example 12

Effects of Sulfate Ion and Zinc Ion on Growth of Cells

Cells were seeded at a density of $3 \times 10^5$ cells/ml and counted after 4 days of growth in media containing in varying amounts of $ZnSO_4$, $ZnCl_2$ or $Na_2SO_4$ in order to determine which ion $Zn^{2+}$ or $SO_4^{2-}$ in zinc sulfate promotes cell growth. Test media supplemented with 25 µm 2-hydroxypyridine-N-oxide and the indicated salts were used to asses the effects of zinc ion and sulfate ion in suspension culture. As shown in FIG. 3, $ZnCl_2$ could effectively substitute for zinc sulfate whereas $Na_2SO_4$ resulted in less cell growth.

Example 13

Evaluation of Flask Volume and Conditioned Media in Transfection Efficiency 293 cells in suspension were grown in the indicated amount of media in 125 ml shake flasks. Results below are averages of duplicate flasks (A-25 ml is for single flask only). The cell densities (at time of set-up) in all cases was $1\times10^6$ viable cells per ml. The DNA and lipid concentrations used were 1 μg and 8 μl respectively per $1\times10^6$ viable cells.

In addition, the effects of conditioned media on transformation were assessed. The results are presented in Table 15.

TABLE 15

| Sample | β-gal expression (ng/~1 × $10^6$ cells) | X-gal stain % transfection efficiency |
|---|---|---|
| A - ml | 9250 | 90-95 |
| A - 15 ml | 8037 | 90-95 |
| A - 20 ml | 4605 | 80 |
| A - 25 ml | 20287 | 99 |
| B - 15 ml | 4224 | 75 |
| B - 15 ml in conditioned media | 8902 | 85-90 |
| B - 15 ml (used LTI Cat. DNA) | 5899 | 75 |
| C - 15 ml | 6965 | 90 |
| C -15 ml in conditioned media | 7312 | 95 |

Note: β-galactosidase production in this experiment is expressed as ng/~$1\times10^6$ cells instead of ng/~$2\times10^6$ cells as in previous experiments.

Flasks set-up in media A were for testing effect of cell suspension volume in the flasks and its effects on transfections. There appears to be no significant difference between a 10 ml and 15 ml volume. However the decline when at 20 ml and then increase at 25 ml is not explained. Also note that 25 ml was not set-up in duplicate.

For samples set-up in B and C the aim was to compare transfectability in fresh media vs. conditioned media. Conditioned media consisted of the media the culture had been growing in until day of transfection set-up. This was done to evaluate whether transfections can be carried out without having to change the culture medium (i.e. spin cells down, re-suspend, etc.). The results show more β-galactosidase produced when in conditioned media for B and comparable results in media C thus supporting the possibility of just adding the lipid-DNA complex to culture when a certain cell density has been reached.

Comparison of the 15 ml samples for A, B and C show no significant difference between A and B and somewhat lower results for C as for as β-gal quantification and similar results for x-gal staining.

Example 14

Effect of Culture Volume on Transfection Efficiency

In order to determine whether the volume of the culture medium affects the efficiency of transfection for a given number of cells, two protocols were tested. The first protocol required the cells to be suspended in a reduced volume of medium and contacted with a nucleic acid and transfection reagent. After an incubation period to allow uptake of the nucleic acid, additional medium was added to bring the culture volume up to a final volume.

The second protocol called for the introduction of a nucleic acid and transfection reagent into the culture at the final volume. Since the second protocol requires one less medium addition step, it requires less manipulation of the cells and less hands-on time.

For both protocols, $3\times10^7$ cells in a final volume of 30 ml medium was used. Nucleic acid:transfection reagent complexes were prepared as follows: 30 μg DNA was added to 1 ml of minimal medium (OPTIMEM, Invitrogen Corporation, Carlsbad, Calif.) 200 μl transfection reagent (LIPOFECTAMINE 2000, Invitrogen Corporation, Carlsbad, Calif.) was added to 1 ml minimal medium. The diluted DNA and transfection reagent were combined, mixed gently and incubated at room temperature for 20 minutes. The complexes were added to the cells and mixed. Cells were incubated at 37° C. on a shaking platform (125 rpm) in 8% $CO_2$/92% air for a total of 48 hours. Aliquots were taken at 24 and 48 hours and assayed for β-galactosidase activity, cell concentration, cell viability and protein content. For protocol 1, cells were initially suspended in 10 ml medium and DNA complexes were added. The cells were incubated 4 hours and then an additional 18 ml medium were added. For protocol 2, cells were suspended in 28 ml medium and DNA complexes were added. The results are presented in Table 16.

TABLE 16

|  | PROTOCOL 1 | PROTOCOL 2 |
|---|---|---|
| 24 hours |  |  |
| mg protein/ $10^6$ cells | 0.8 | 0.9 |
| μg β-gal/ $10^6$ cells | 22.7 | 25.0 |
| μg β-gal/ mg protein | 28.7 | 28.7 |
| expected mg β-gal/L cells | 22.7 | 25 |
| 48 hours |  |  |
| mg protein/ $10^6$ cells | 1.1 | 1.1 |
| μg β-gal/ $10^6$ cells | 50.1 | 52.9 |
| μg β-gal/ mg protein | 46.4 | 46.8 |
| expected mg β-gal/L cells | 50.1 | 52.9 |
| mg β-gal/ 30 ml culture | 1.5 | 1.6 |

As seen in Table 16, initially culturing the cells in a reduced volume in order to facilitate uptake of nucleic acid by the cells did not increase the overall yield of β-galactosidase.

Example 15

Effect of Transfection Reagent Concentration on Transfection Efficiency

Since no advantage was seen in incubating the nucleic acid complexes with cells in a reduced volume, protocol 2 was used in the following experiment. In order to assess the effects of varying the amount of transfection reagent transformations were conducted using 100 μl, 150 μl and 200 μl of LIPOFECTAMINE 2000. The indicated amount of transfection reagent was diluted in 1 ml minimal medium and 30 μg DNA was diluted in 1 ml medium as described above. The dilutions were combined and mixed gently and incubated 20 minutes at room temperature. The nucleic acid complexes were added to $3\times10^7$ cells in 28 ml of medium. Aliquots were taken at 25 hours and 49 hours and assayed as above. The results are presented in Table 17.

TABLE 17

| | 24 HOURS | | 48 HOURS | |
|---|---|---|---|---|
| | live cells/ml % viable | mg β-gal/ 30 ml culture | live cells/ml % viable | mg β-gal/ 30 ml culture |
| untransfected control | 2.3 × 10⁶ 84% | 0 | 2.4 × 10⁶ 69% | 0 |
| 100 µl LIPOFECTA-MINE 2000 | 1.2 × 10⁶ 79% | 0.6 | 1.7 × 10⁶ 69% | 1.2 |
| 150 µl LIPOFECTA-MINE 2000 | 1.1 × 10⁶ 74% | 0.5 | 1.6 × 10⁶ 65% | 1.3 |
| 150 µl LIPOFECTA-MINE 2000 + butyrate | 1.7 × 10⁶ 82% | 1.4 | 1.3 × 10⁶ 61% | 2.7 |
| 200 µl LIPOFECTA-MINE 2000 | 1.2 × 10⁶ 70% | 0.6 | 1.4 × 10⁶ 62% | 1.3 |

The amount of transfection reagent did not seem to dramatically affect the expression levels of β-galactosidase (compare 1.2 mg/30 ml of culture at 100 µl transfection reagent to 1.3 mg/30 ml of culture at 200 µl of transfection reagent). In contrast, the presence of butyrate in the culture medium more than doubled the production of β-galactosidase from 1.3 mg/30 ml of culture to 2.7 mg/30 ml of culture.

Example 16

The effect of PL-1, PL-2 and PL000458 media on cell growth and viability for 293 cells was determined. 293-F cells were seeded at 3×10⁵ cell/ml initial density (in 30 ml cultures) in shaker flasks (8% $CO_2$, 37° C., 125 rpm). Viability and cell density were measured approximately every 24 hours. The results are shown in FIGS. 4A-D.

Having now fully described the present invention in some detail by way of illustration and example for purposes of clarity of understanding, it will be obvious to one of ordinary skill in the art that the same can be performed by modifying or changing the invention within a wide and range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertains, and are herein incorporated by reference to the same extent as if each individual publication, patent or patent application was specifically and individually indicated to be incorporated by reference.

What is claimed is:

1. A method for introducing a nucleic acid into a 293F cell under serum-free suspension culture conditions, said method comprising:
   (a) culturing the 293F cell in the serum-free conditions comprising serum-free cell culture medium, wherein the cell culture medium supports the introduction of the nucleic acid into the 293F cell and also supports cultivation of the 293F cell subsequent to introduction of the nucleic acid, wherein the nucleic acid encodes a protein and is operably linked to a promoter;
   (b) introducing a lipid aggregate comprising the nucleic acid into the cell culture medium in which the 293F cell is cultured under conditions sufficient to introduce the nucleic acid into the 293F cell; and
   (c) cultivating the 293F cell into which the nucleic acid has been introduced in the culture medium under conditions sufficient to express the protein from the nucleic acid,
   wherein during step (b) the culture medium is not replenished, replaced or supplemented for at least 48 hours; and
   wherein cultivation of the 293F cell in step (c) is accomplished in a volume of the culture medium that is about the same or up to about 2 times the volume of the culture medium in which step (b) occurred.

2. The method of claim 1, wherein the lipid aggregate comprises a cationic lipid.

* * * * *